United States Patent [19]

Santamaria et al.

[11] Patent Number: 5,578,443
[45] Date of Patent: Nov. 26, 1996

[54] DNA SEQUENCE-BASED HLA TYPING METHOD

[75] Inventors: Pedro Santamaria, Minneapolis; Michael T. Boyce-Jacino, Saint Paul; Jose J. Barbosa, Roseville; Stephen S. Rich, Saint Paul; Anthony J. Faras, Long Lake, all of Minn.

[73] Assignee: Regents of the University of Minnesota, Minn.

[21] Appl. No.: 665,960

[22] Filed: Mar. 6, 1991

[51] Int. Cl.$^6$ .............................. C12Q 1/48; C12Q 1/68; C12P 19/34; C12N 15/11

[52] U.S. Cl. .............................. 435/6; 435/15; 435/91.1; 435/91.2; 435/91.21; 435/91.5; 536/23.1; 536/24.3; 536/24.33; 935/8; 935/17; 935/18; 935/77; 935/78

[58] Field of Search .................................. 435/6, 15, 91, 435/91.1, 91.2, 91.21, 91.5; 536/27, 23.1, 24.33, 24.3; 935/8, 17, 18, 77, 78

[56] References Cited

U.S. PATENT DOCUMENTS

| | | | |
|---|---|---|---|
| 4,582,788 | 4/1986 | Erlich | 435/6 |
| 4,683,195 | 7/1987 | Mullis et al. | 435/6 |
| 4,683,202 | 7/1987 | Mullis | 435/91 |
| 4,835,098 | 5/1989 | Orr et al. | 435/6 |

FOREIGN PATENT DOCUMENTS

| | | |
|---|---|---|
| 3927467 | 2/1991 | Germany. |
| 4006974 | 9/1991 | Germany. |
| WO89/11547 | 11/1989 | WIPO. |

OTHER PUBLICATIONS

Gyllensten in *PCR Technology*, H. Erlich editor, Stockton Press (1989) at p. 47.

*Biotechniques*, vol. 7, No. 4, issued Apr. 1989, K. B. Gorman et al. "Simplified Method for Selective Amplification and Direct Sequencing of cDNAs" pp. 326–329, see entire document.

*Proceedings of the National Academy of Science USA*, vol. 85, issued Jan. 1988, D. R. Engelke et al., "Direct Sequencing of Enzymatically Amplified Human Genomic DNA", pp. 544–548, see entire document.

*Clinical Chemistry*, vol. 38, No. 11, issued Nov. 1989, L. J. McBride et al., "Automated DNA Sequencing Methods Involving Polymerase Chain Reaction", pp. 2196–2201, see especially pp. 2200–2201.

P. Parham, *Nature*, 350, 111 (1991).

G. Nepom, *Immunol. Res.*, 8, 16 (1989).

E. Stoflet et al., *Science*, 239, 491 (1988).

G. Thomson, *The Handbook of Experimental Immunology*, 3, Chapter 102, (1986).

L. Smith et al., *The Handbook of Experimental Immunology*, 3, Chapter 87 (1986).

Marsh et al., "Nomenclature for factors of the HLA system, 1989", *Immunogenetics*, 31:131 (1990).

F. Bach et al., "The HLA class II genes and products: the HLA–D region", *Immuno. Today*, 6:89 (1985).

(List continued on next page.)

*Primary Examiner*—Robert A. Wax
*Assistant Examiner*—Rebecca Prouty

[57] ABSTRACT

The present invention provides a process for determining genotypes in highly polymorphic systems by polymerase chain reaction amplification of cDNA or genomic DNA and direct sequencing polymerase chain reaction products using oligonucleotide primers. More specifically, Class II and Class I HLA genotypes can be unambiguously determined in any subject in 16–24 hours by direct sequencing of DRB, DQB, DQA, DPB, DPA, HLA-A, HLA-B and HLA-C-transcripts enzymatically amplified using a limited number of non-allele-specific oligonucleotides. Total cellular RNA from peripheral blood mononuclear cells is reverse transcribed using antisense primers, specific for different locus (DQB, DQA, DPA or DPB) or group of loci (DRB1–5, or HLA-A and HLA-B and HLA-C). The synthesized cDNA molecules are then enzymatically amplified using different combinations of oligonucleotides for each locus and directly sequenced with Taq polymerase using an internal oligonucleotide. The sequenced genes are then analyzed.

39 Claims, 4 Drawing Sheets

OTHER PUBLICATIONS

R. Zinkernagel et al., "Restriction of in vitro T cell–mediated cytotoxicity in lymphocytic chloriomeningitis within a syngeneic or semiallogeneic system", *Nature*, 248:701 (1974).

F. Bach et al., "The Major Histocompatibility Complex—Genetics and Biology", *New Eng. J. of Med.*, 295:806 (1976).

Bidwell, "DNA–RFLP analysis and genotyping of HLA–DR and DG antigens", *Immunology Today*, 9:18 (1988).

J. Tiercy et al., "Identification and distribution of three serologically undetected alleles of HLA–DR by oligonucleotide–DNA typing analysis", *Proc. Natl. Acad. Sci. USA*, 85:198 (1988).

P. Erlich, *PCR Techniques*, (1989).

Todd et al., "HLA–DQ gene contributtes to susceptibility and resistance to insulin–dependent diabetes mellitus", *Nature*, 329:599 (1987).

Saiki et al., "Enzymatic Amplification of –Globin Genomic Sequences and Restriction Sittte Analysis for Diagnosis of Sickle Cell Anemia", *Science*, 230:1350 (1985).

K. Mullis et al., "Specific Synthesis of DNA in Vitro via a Polymerase–Catalyzed Chain Reaction", *Methods Enzymol.*, 155:335 (1987).

Saiki et al., "Analysis of enzymatically amplified –globin and HLA–DQA DNA with allele–specific oligonucleotide probes", *Nature*, 324:163 (1986).

Scharf et al., "Direct Cloning and Sequence Analysis of Enzymatically Amplified Genomic Sequences", *Science*, 233:1076 (1986).

Gyllenstein et al., "Generation of single–stranded DNA by the polymerase chain reaction and its application to direct sequencing of the HLA–DQA locus", Proc. Natl. Acad. Sci. USA 85:7652 (1988).

Brown et al., "Chemical Synthesis and Cloning of a Pyrosine cDNA Gene", *Meth. in Enzymol.*, 68:109 (1979).

Caruthers et al., "Chemical Synthesis of Deoxyoligonucleotides by the Phosphoramidite Method", *Methods Enzymol.*, 154:287 (1987).

Schulhof et al., "The final deprotection step in oligonucleotide synthesis is reduced to a mild and rapid ammonia treatment by using labile base–protecting groups", *Nucl. Acid Res.*, 15:397 (1987).

Dupont, *Hum. Immunol.*, 26:3 (1984).

Chirgwin et al., "Isolation of Biologically Active Ribonucleic Acid from Sources Enriched in Ribonuclease", *Biochemistry*, 18:5247 (1979).

Gough, "Rapid and Quantitative Preparation of Cytoplasmic RN from Small Numbers of Cells", *Anal. Biochem*, 173:93 (1988).

Knowles, *Immunobiology of the HLA*, vol. I, 365–380 (1989).

Gregerson et al., *Proc. Nat'l Acad. Sci.*, 83, 2642–46 (1986).

Kao et al., *J. Immunol.*, 142, 1743 (1989).

Merryman et al., *J. Immunol.*, 140, 2447–52 (1988).

Merryman et al., *J. Immunol.*, 143, 2068–73 (1989).

S. Marsh et al., "HLA–DRB nucleotide sequences, 1990", *Immunogenetics*, 31:141 (1990).

Johns et al., "Purification of Human Genomic DNA from Whole Blood Using Sodium Perchlorate in Place of Phenol", *Anal. Biochem.*, 180:276 (1989).

R. Higuchi, "Simple and Rapid Preparation of Samples for PCR", *PCR Technology*, (1989).

M. A. Innis et al. Proc. Natl. Acad. Sci. 85:9436–9440 (Dec. 1988).

U. B. Gyllensten. Proc. Natl. Acad. Sci 85:7652–7656 (1988).

Begovich, A. B. et al. "A specific HLA–DPB allele is associated . . . " Proc. Natl. Acad. Sci. 86:9489–9493 (Dec. 1989).

Bugawan, T. L. et al. "Analysis of HLA–DP Allelic . . . " J. Immunology 141(12):4024–4030 (Dec. 1988).

Lee, J. S. et al. "Sequence polymorphism of HLA–DP . . . " Immunogenetics 29:346–349 (May 1989).

Lair, B. et al. "A newly characterized HLA–DPB Chain Allele." J. Immunology 141(4) 1353–1357 (Aug. 1988).

Gyllensten, U. B. et al. "Allelic diversification at the Class I . . . " Proc. Natl. Acad. Sci 87:1835–1839 (Mar. 1990).

Auffray, C. et al. "cDNA clone for the heavy chain . . . " Proc. Natl. Acad. Sci 79:6337–6341 (Oct. 1982).

Uryu, N. et al. "No Difference in the Nucleotide Sequence . . . " Human Immunology 24:175–181 (Mar. 1989).

Wai, S. et al. "Full length DQB cDNA Sequences of . . . " Human Immunology 27:305–322 (Jul. 1990).

Boss, J. M. "Cloning and sequence analysis of the . . . " Proc. Natl. Acad. Sci 81:5199–5203 (Aug. 1984).

Scharf, S. J. et al. "Specific HLA–DQB and HLA–DRBI . . . " Proc. Natl. Acad. Sci. 86:6215–6219 (Aug. 1989).

Briata, P. et al. "Alternative splicing of HLA–DQB transcripts . . . " Proc. Natl. Acad. Sci 86:1003–1007 (Feb. 1989).

Larhammar, D. et al. "Exon–intron organization and complete . . . " Proc. Natl. Acad. Sci 80:7313–7317 (Dec. 1983).

Schenning et al. "Both α and β chains of HLA–DC Class II . . . " EMBO J. 3(2): 447–452 (Feb. 1984).

Schiffenbauer, J. et al. "Complete Sequence of the HLA DQα . . . " J. Immunology 139:228–233 (Jul. 1987).

Morinchi, J. et al. "Nucleotide sequence of an HLA DQα chain . . . " Proc. Natl. Acad. Sci 82:3420–3424 (May 1985).

Trousdale, J. "Structure, Sequence and Polymorphism in . . . " Immunological Rev. 85:5–43 (Jul. 1985).

Gorman, K. B. et al. "Simplified Method for Selective Amplification . . . " Biotechniques 7(4):326–329 (Apr. 1989).

McBride, L. J. et al. "Automated DNA Sequencing Methods . . . " Clinical Chemistry 35(11):2196–2201 (Nov. 1989).

Engelke, D. R. et al. "Direct Sequencing of enzymatically . . . " Proc. Natl. Acad. Sci 85:544–548 (Jan. 1988).

Wong, C. et al. "Characterization of β–thalassaemia mutations . . . " Nature 320:384–386 (Nov.(1987).

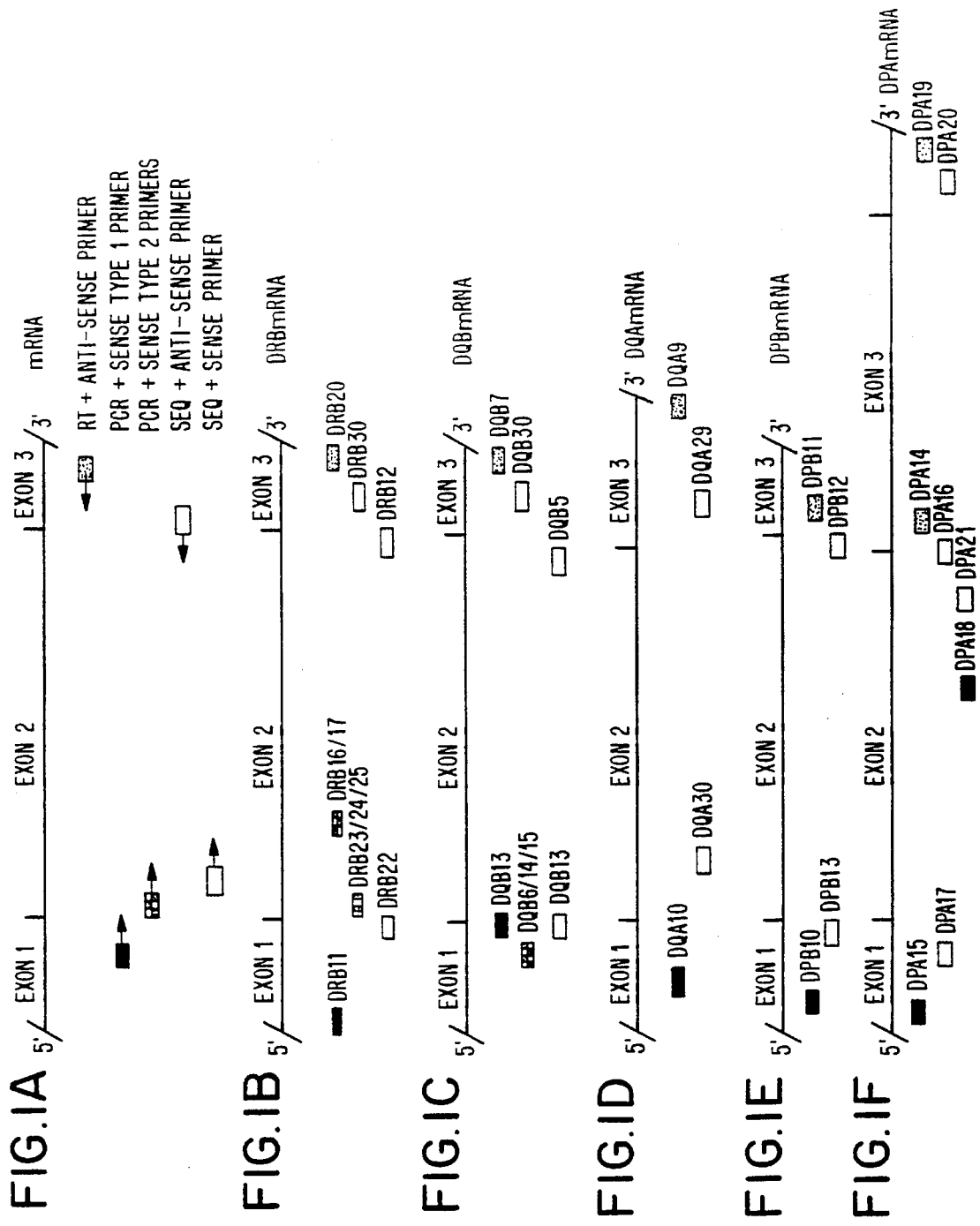

SEQUENCE LISTING ( 1 ) GENERAL INFORMATION:

( i i i ) NUMBER OF SEQUENCES: 49

( 2 ) INFORMATION FOR SEQ ID NO: 1:

( i ) SEQUENCE CHARACTERISTICS:
( A ) LENGTH: 21 base pairs
( B ) TYPE: Nucleic Acid
( C ) STRANDEDNESS: Single
( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
( A ) NAME/KEY: Oligonucleotide Primer DQB7
( B ) LOCATION: Anneals to codons 105 to 111 of the
DQB1 transcript of HLA class II ( x i ) SEQUENCE DESCRIPTION: SEQ ID NO: 1:

G GTG GTT GAG GGC CTC TGT CC      21

( 2 ) INFORMATION FOR SEQ ID NO: 2:

( i ) SEQUENCE CHARACTERISTICS:
( A ) LENGTH: 21 base pairs
( B ) TYPE: Nucleic Acid
( C ) STRANDEDNESS: Single
( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
( A ) NAME/KEY: Oligonucleotide Primer DRB20
( B ) LOCATION: Anneals to codons 105 to 111 of the
DRB1, DRB3, DRB4 and DRB5 transcripts of HLA
class II ( x i ) SEQUENCE DESCRIPTION: SEQ ID NO: 2:

GTG CTG CAG GGG CTG GGT CTT      21

( 2 ) INFORMATION FOR SEQ ID NO: 3:

( i ) SEQUENCE CHARACTERISTICS:
( A ) LENGTH: 22 base pairs
( B ) TYPE: Nucleic Acid
( C ) STRANDEDNESS: Single
( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
( A ) NAME/KEY: Oligonucleotide Primer DQA9
( B ) LOCATION: Anneals to codons 148 to 155 of the DQA1 transcript of HLA class II ( x i ) SEQUENCE DESCRIPTION: SEQ ID NO: 3:

```
                GGT  GAG  GTT  ACT  GAT  CTT  GAA  G                    2 2
```

( 2 ) INFORMATION FOR SEQ ID NO: 4:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DQB13
        ( B ) LOCATION: Anneals to codons 1 to 7 of the
            DQB1 transcript of HLA class II ( x i ) SEQUENCE DESCRIPTION: SEQ ID NO: 4:

```
                AGA  GAC  TCT  CCC  GAG  GAT  TTC                       2 1
                Arg  Asp  Ser  Pro  Glu  Asp  Phe
                 1                   5
```

( 2 ) INFORMATION FOR SEQ ID NO: 5:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DBR22
        ( B ) LOCATION: Anneals to codons -4 to +3 of the
            DRB1, DRB3, DRB4 and DRB5 transcripts of HLA
            class II ( x i ) SEQUENCE DESCRIPTION: SEQ ID NO: 5:

```
                CTG  GCT  TTG  GCT  GGG  GAC  ACC                       2 1
                Leu  Ala  Leu  Ala  Gly  Asp  Thr
                               - 1   1
```

( 2 ) INFORMATION FOR SEQ ID NO: 6:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived 5,578,443

33

-continued ( i x ) FEATURE:
    ( A ) NAME/KEY: Oligonucleotide Primer DRB11
    ( B ) LOCATION: Anneals to codons -33 to -26 of the
        DRB1, DRB3, DRB4 and DRB5 transcripts of HLA
        class II ( x i ) SEQUENCE DESCRIPTION: SEQ ID NO: 6:

```
TG TTC TCC AGC ATG GTG TGT C                          21
   Phe Ser Ser Met Val Cys Leu
       -30
```

( 2 ) INFORMATION FOR SEQ ID NO: 7:

( i ) SEQUENCE CHARACTERISTICS:
        ( A ) LENGTH: 20 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DQA10
        ( B ) LOCATION: Anneals to codons -10 to -4 of the
            DQA1 transcript of HLA class II ( x i ) SEQUENCE DESCRIPTION: SEQ ID NO: 7:

```
CTG TCC TCC GTG ATG AGC CC                            20
Leu Thr Thr Val Met Ser Pro
-10                     -5
```

( 2 ) INFORMATION FOR SEQ ID NO: 8:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DQB932
        ( B ) LOCATION: Anneals to codons 88 to 94 of the
            DQB1 transcript of HLA class II ( x i ) SEQUENCE DESCRIPTION: SEQ ID NO: 8:

```
TCG CCT CTG CAG GGT CGC GCG                           21
```

( 2 ) INFORMATION FOR SEQ ID NO: 9:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
    ( A ) NAME/KEY: Oligonucleotide Primer DQB931
    ( B ) LOCATION: Anneals to codons 11 to 17 of the
        DQB1 transcript of HLA class II ( x i ) SEQUENCE DESCRIPTION: SEQ ID NO: 9:

```
        TTT  AAG  GGC  ATG  TGC  TAC  TTC              21
        Phe  Lys  Gly  Met  Cys  Tyr  Phe
                           15
```

( 2 ) INFORMATION FOR SEQ ID NO: 10:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DQB30
        ( B ) LOCATION: Anneals to codons 97 to 104 of the
            DQB1 transcript of HLA class II ( x i ) SEQUENCE DESCRIPTION: SEQ ID NO: 10:

```
           A  TGG  GGA  GAT  GGT  CAC  TGT  GG         21
```

( 2 ) INFORMATION FOR SEQ ID NO: 11:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DRB30
        ( B ) LOCATION: Anneals to codons 97 to 103 of the
            DRB1, DRB3, DRB4 and DRB5 transcripts of HLA
            class II ( x i ) SEQUENCE DESCRIPTION: SEQ ID NO: 11:

```
             AGG  ATA  CAC  AGT  CAC  CTT  AGG         21
```

( 2 ) INFORMATION FOR SEQ ID NO: 12:

( i ) SEQUENCE CHARACTERISTICS:
        ( A ) LENGTH: 18 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
    ( A ) NAME/KEY: Oligonucleotide Primer DQB5
    ( B ) LOCATION: Anneals to codons 78 to 83 of the
        DQB1 transcript of HLA class II ( x i ) SEQUENCE DESCRIPTION: SEQ ID NO: 12:

GTA GTT GTG TCT GCA CAC         18

( 2 ) INFORMATION FOR SEQ ID NO: 13:

( i ) SEQUENCE CHARACTERISTICS:
        ( A ) LENGTH: 20 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DRB12
        ( B ) LOCATION: Anneals to codons 87 to 94 of the
            DRB1, DRB3, DRB4 and DRB5 transcripts of HLA
            class II ( x i ) SEQUENCE DESCRIPTION: SEQ ID NO: 13:

G CCG CTG CAC TGT GAA GCT C         20

( 2 ) INFORMATION FOR SEQ ID NO: 14:

( i ) SEQUENCE CHARACTERISTICS:
        ( A ) LENGTH: 23 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DQA29
        ( B ) LOCATION: Anneals to codons 82 to 89 of the
            DQA1 transcript of HLA class II ( x i ) SEQUENCE DESCRIPTION: SEQ ID NO: 14:

CAC GGT TCC GGT AGC AGC GGT AG         23

( 2 ) INFORMATION FOR SEQ ID NO: 15:

( i ) SEQUENCE CHARACTERISTICS:
        ( A ) LENGTH: 18 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment (vi) ORIGINAL SOURCE: Synthetically Derived (ix) FEATURE:
    (A) NAME/KEY: Oligonucleotide Primer DQA30
    (B) LOCATION: Anneals to codons 19 to 24 of the
        DQA1 transcript of HLA class II (xi) SEQUENCE DESCRIPTION: SEQ ID NO: 15:

```
        TAC GGT CCC TCT GGC CAG                 18
        Tyr Gly Pro Ser Glu Gln
             20
```

(2) INFORMATION FOR SEQ ID NO: 16:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
        (A) NAME/KEY: Oligonucleotide Primer DRB1400
        (B) LOCATION: Anneals to codons 38 to 45 of the
            DRB1, DRB3, DRB4 and DRB5 transcripts of HLA
            class II (xi) SEQUENCE DESCRIPTION: SEQ ID NO: 16:

```
      G CGC TTC GAC AGC GAC GTG G               20
      Val Arg Phe Asp Ser Asp Val Gly
              40                      45
```

(2) INFORMATION FOR SEQ ID NO: 17:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
        (A) NAME/KEY: Oligonucleotide Primer DRB1401
        (B) LOCATION: Anneals to codons 98 to 104 of the
            DRB1*0701-2 transcript of HLA class II (xi) SEQUENCE DESCRIPTION: SEQ ID NO: 17:

```
        GAG GTG ACT GTG TAT CCT GAC             21
        Glu Val Thr Val Tyr Pro Asp
                100
```

(2) INFORMATION FOR SEQ ID NO: 18:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (ii) MOLECULE TYPE: Genomic DNA (iv) ANTI-SENSE: yes (v) FRAGMENT TYPE: Internal Fragment (vi) ORIGINAL SOURCE: Synthetically Derived (ix) FEATURE:
(A) NAME/KEY: Oligonucleotide Primer DQB1402
(B) LOCATION: Anneals to codons 142 to 148 of the DRB1, DRB3, DRB4 and DRB5 transcripts of HLA class II (xi) SEQUENCE DESCRIPTION: SEQ ID NO: 18:

GAT CAG GCC TGT GGA CAC CAC  21

(2) INFORMATION FOR SEQ ID NO: 19:

(i) SEQUENCE CHARACTERISTICS:
(A) LENGTH: 21 base pairs
(B) TYPE: Nucleic Acid
(C) STRANDEDNESS: Single
(D) TOPOLOGY: Linear (ii) MOLECULE TYPE: Genomic DNA (iv) ANTI-SENSE: yes (v) FRAGMENT TYPE: Internal Fragment (vi) ORIGINAL SOURCE: Synthetically Derived (ix) FEATURE:
(A) NAME/KEY: Oligonucleotide Primer DQB1403
(B) LOCATION: Anneals to codons 127 to 133 of the DRB1, DRB3, DRB4 and DRB5 transcripts of HLA class II (xi) SEQUENCE DESCRIPTION: SEQ ID NO: 19:

CCG GAA CCA CCT GAC TTC AAT  21

(2) INFORMATION FOR SEQ ID NO: 20:

(i) SEQUENCE CHARACTERISTICS:
(A) LENGTH: 21 base pairs
(B) TYPE: Nucleic Acid
(C) STRANDEDNESS: Single
(D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
(A) NAME/KEY: Oligonucleotide Primer DQB1406
(B) LOCATION: Anneals to bp18-38 to intron 33 of the DRB1, DRB3, DRB4 and DRB5 transcripts of HLA class II (xi) SEQUENCE DESCRIPTION: SEQ ID NO: 20:

GCCAAGAGTG GGCCTCGCAG C  21

(2) INFORMATION FOR SEQ ID NO: 21:

(i) SEQUENCE CHARACTERISTICS:
(A) LENGTH: 21 base pairs
(B) TYPE: Nucleic Acid
(C) STRANDEDNESS: Single
(D) TOPOLOGY: Linear (ii) MOLECULE TYPE: Genomic DNA (iv) ANTI-SENSE: yes (v) FRAGMENT TYPE: Internal Fragment (vi) ORIGINAL SOURCE: Synthetically Derived (ix) FEATURE:
    (A) NAME/KEY: Oligonucleotide Primer DRB825
    (B) LOCATION: Anneals to codons 79 to 85 of the
        DRB1, DRB3, DRB4 and DRB5 transcripts of HLA
        class II (xi) SEQUENCE DESCRIPTION: SEQ ID NO: 21:

```
          AAC  CCC  GTA  GTT  GTG  TCT  GCA                    21
```

(2) INFORMATION FOR SEQ ID NO: 22:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
        (A) NAME/KEY: Oligonucleotide Primer DRB824
        (B) LOCATION: Anneals to codons 1 to 7 of the
            DRB1, DRB3, DRB4 and DRB5 transcripts of HLA
            class II (xi) SEQUENCE DESCRIPTION: SEQ ID NO: 22:

```
          GGG  GAC  ACC  CGA  CCA  CGT  TTC                    21
          Gly  Ala  Thr  Arg  Pro  Arg  Phe
           1                   5
```

(2) INFORMATION FOR SEQ ID NO: 23:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
        (A) NAME/KEY: Oligonucleotide Primer DPB10
        (B) LOCATION: Anneals to codons -19 to -13 of the
            DPB1 transcript of HLA class II (xi) SEQUENCE DESCRIPTION: SEQ ID NO: 23:

```
          CGG  ACA  GTG  GCT  CTG  ACG  GCG                    21
          Arg  Thr  Val  Ala  Leu  Tyr  Ala
                              -15
```

(2) INFORMATION FOR SEQ ID NO: 24:

(i) SEQUENCE CHARACTERISTICS:

( A ) LENGTH: 21 base pairs
( B ) TYPE: Nucleic Acid
( C ) STRANDEDNESS: Single
( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
( A ) NAME/KEY: Oligonucleotide Primer DPB11
( B ) LOCATION: Anneals to codons 105 to 111 of the
DPB1 transcript of HLA class II ( x i ) SEQUENCE DESCRIPTION: SEQ ID NO: 24:

GTT GTG GTG CTG CAA GGG CCC    21

( 2 ) INFORMATION FOR SEQ ID NO: 25:

( i ) SEQUENCE CHARACTERISTICS:
( A ) LENGTH: 21 base pairs
( B ) TYPE: Nucleic Acid
( C ) STRANDEDNESS: Single
( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
( A ) NAME/KEY: Oligonucleotide Primer DPB12
( B ) LOCATION: Anneals to codons 97 to 103 of the
DPB1 transcript of HLA class II ( x i ) SEQUENCE DESCRIPTION: SEQ ID NO: 25:

CTT GGA GGG GGA AAC ATT CAC    21

( 2 ) INFORMATION FOR SEQ ID NO: 26:

( i ) SEQUENCE CHARACTERISTICS:
( A ) LENGTH: 21 base pairs
( B ) TYPE: Nucleic Acid
( C ) STRANDEDNESS: Single
( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
( A ) NAME/KEY: Oligonucleotide Primer DPB13
( B ) LOCATION: Anneals to codons -5 to +2 of the
DPB1 transcript of HLA class II ( x i ) SEQUENCE DESCRIPTION: SEQ ID NO: 26:

TCT GTG GTC CAG GGC AGG GCC    21
Ser Val Val Gln Gly Arg Ala
-5              -1   1

( 2 ) INFORMATION FOR SEQ ID NO: 27:

( i ) SEQUENCE CHARACTERISTICS:

(A) LENGTH: 21 base pairs
(B) TYPE: Nucleic Acid
(C) STRANDEDNESS: Single
(D) TOPOLOGY: Linear (i i) MOLECULE TYPE: Genomic DNA (i v) ANTI-SENSE: no (v) FRAGMENT TYPE: Internal Fragment (v i) ORIGINAL SOURCE: Synthetically Derived (i x) FEATURE:
    (A) NAME/KEY: Oligonucleotide Primer DPB14
    (B) LOCATION: Anneals to bp-42/-46 to intron 2 of
        the DPB1 transcript of HLA class II (x i) SEQUENCE DESCRIPTION: SEQ ID NO: 27:

AGAGGGAGAA AGAGGATTAG A        21

(2) INFORMATION FOR SEQ ID NO: 28:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (i i) MOLECULE TYPE: Genomic DNA (i v) ANTI-SENSE: no (v) FRAGMENT TYPE: Internal Fragment (v i) ORIGINAL SOURCE: Synthetically Derived (i x) FEATURE:
    (A) NAME/KEY: Oligonucleotide Primer DPB15
    (B) LOCATION: Anneals to bp39-59 to intron 3 of
        the DPB1 transcript of HLA class II (x i) SEQUENCE DESCRIPTION: SEQ ID NO: 28:

GCCCTGGGCA CGGGCCCGCG G        21

(2) INFORMATION FOR SEQ ID NO: 29:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (i i) MOLECULE TYPE: Genomic DNA (i v) ANTI-SENSE: no (v) FRAGMENT TYPE: Internal Fragment (v i) ORIGINAL SOURCE: Synthetically Derived (i x) FEATURE:
    (A) NAME/KEY: Oligonucleotide Primer DPB16
    (B) LOCATION: Anneals to bp1-21 to intron 3 of
        the DPB1 transcript of HLA class II (x i) SEQUENCE DESCRIPTION: SEQ ID NO: 29:

CGGCCCAAAG CCCTCACTCA C        21

(2) INFORMATION FOR SEQ ID NO: 30:

(i) SEQUENCE CHARACTERISTICS:
        (A) LENGTH: 21 base pairs
        (B) TYPE: Nucleic Acid (C) STRANDEDNESS: Single
(D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
(A) NAME/KEY: Oligonucleotide Primer DPB17
(B) LOCATION: Anneals to bp-6/-26 to intron 2 of the DPB1 transcript of HLA class II (xi) SEQUENCE DESCRIPTION: SEQ ID NO: 30:

CGCTCATGTC CGCCCCCTCC C  21

(2) INFORMATION FOR SEQ ID NO: 31:

(i) SEQUENCE CHARACTERISTICS:
(A) LENGTH: 21 base pairs
(B) TYPE: Nucleic Acid
(C) STRANDEDNESS: Single
(D) TOPOLOGY: Linear (ii) MOLECULE TYPE: Genomic DNA (iv) ANTI-SENSE: yes (v) FRAGMENT TYPE: Internal Fragment (vi) ORIGINAL SOURCE: Synthetically Derived (ix) FEATURE:
(A) NAME/KEY: Oligonucleotide Primer DPA14
(B) LOCATION: Anneals to codons 104 to 110 of the DPA1 transcript of HLA class II (xi) SEQUENCE DESCRIPTION: SEQ ID NO: 31:

GTC AAT GTG GCA GAT GAG GGT  21

(2) INFORMATION FOR SEQ ID NO: 32:

(i) SEQUENCE CHARACTERISTICS:
(A) LENGTH: 21 base pairs
(B) TYPE: Nucleic Acid
(C) STRANDEDNESS: Single
(D) TOPOLOGY: Linear (ii) MOLECULE TYPE: Genomic DNA (iv) ANTI-SENSE: yes (v) FRAGMENT TYPE: Internal Fragment (vi) ORIGINAL SOURCE: Synthetically Derived (ix) FEATURE:
(A) NAME/KEY: Oligonucleotide Primer DPA15
(B) LOCATION: Anneals to codons -17 to -23 of the DPA1 transcript of HLA class II (xi) SEQUENCE DESCRIPTION: SEQ ID NO: 32:

CAT ATC AGA GCT GTG ATC TTG  21

(2) INFORMATION FOR SEQ ID NO: 33:

(i) SEQUENCE CHARACTERISTICS:
(A) LENGTH: 21 base pairs
(B) TYPE: Nucleic Acid
(C) STRANDEDNESS: Single
(D) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
    ( A ) NAME/KEY: Oligonucleotide Primer DPA16
    ( B ) LOCATION: Anneals to codons 88 to 94 of the
        DPA1 transcript of HLA class II ( x i ) SEQUENCE DESCRIPTION: SEQ ID NO: 33:

```
CTT GGG AAA CAC GGT CAC CTC                    21
```

( 2 ) INFORMATION FOR SEQ ID NO: 34:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DPA17
        ( B ) LOCATION: Anneals to codons -3 to -9 of the
            DPA1 transcript of HLA class II ( x i ) SEQUENCE DESCRIPTION: SEQ ID NO: 34:

```
CTG CTG AGT CTC CGA GGA GCT                    21
Leu Leu Ser Leu Arg Gly Ala
            - 5
```

( 2 ) INFORMATION FOR SEQ ID NO: 35:

( i ) SEQUENCE CHARACTERISTICS:
        ( A ) LENGTH: 20 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DPA10
        ( B ) LOCATION: Anneals to bp-69/-50 of intron 2 of
            the DPA1 transcript of HLA class II ( x i ) SEQUENCE DESCRIPTION: SEQ ID NO: 35:

```
CTCTAGCTTT GACCACTTGC                          20
```

( 2 ) INFORMATION FOR SEQ ID NO: 36:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
    ( A ) NAME/KEY: Oligonucleotide Primer DPA11
    ( B ) LOCATION: Anneals to bp55-71 to intron 3 of
        the DPA1 transcript of HLA class II ( x i ) SEQUENCE DESCRIPTION: SEQ ID NO: 36:

```
            AGTCTGAGGG TGGCAGAGAG G                        21
```

( 2 ) INFORMATION FOR SEQ ID NO: 37:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DPA12
        ( B ) LOCATION: Anneals to codons 76 to 82 of the
            DPA1 transcript of HLA class II ( x i ) SEQUENCE DESCRIPTION: SEQ ID NO: 37:

```
            GGC CTG AGT GTG GTT GGA ACG                    21
```

( 2 ) INFORMATION FOR SEQ ID NO: 38:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DPA18
        ( B ) LOCATION: Anneals to codons 59 to 65 of the
            DPA1 transcript of HLA class II ( x i ) SEQUENCE DESCRIPTION: SEQ ID NO: 38:

```
            CTG GCT AAC ATT GCT ATA TTG                    21
            Leu Ala Asn Ile Ala Ile Leu
                 60                  65
```

( 2 ) INFORMATION FOR SEQ ID NO: 39:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
    ( A ) NAME/KEY: Oligonucleotide Primer DPA19
    ( B ) LOCATION: Anneals to codons 222 to 228 of the
        DPA1 transcript of HLA class II ( x i ) SEQUENCE DESCRIPTION: SEQ ID NO: 39:

```
            GGT CCC CTG GGC CCG GGG GTC                    21
```

( 2 ) INFORMATION FOR SEQ ID NO: 40:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DPA20
        ( B ) LOCATION: Anneals to codons 214 to 220 of the
            DPA1 transcript of HLA class II ( x i ) SEQUENCE DESCRIPTION: SEQ ID NO: 40:

```
            GCC AGA ACG CAG AGA CTT TAT                    21
```

( 2 ) INFORMATION FOR SEQ ID NO: 41:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
        ( A ) NAME/KEY: Oligonucleotide Primer DPA21
        ( B ) LOCATION: Anneals to codons 68 to 74 of the
            DPA1 transcript of HLA class II ( x i ) SEQUENCE DESCRIPTION: SEQ ID NO: 41:

```
            AAC TTG AAT ACC TTG ATC CAG                    21
            Asn Leu Asn Thr Leu Ile Gln
                         70
```

( 2 ) INFORMATION FOR SEQ ID NO: 42:

( i ) SEQUENCE CHARACTERISTICS:
        ( A ) LENGTH: 20 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
    ( A ) NAME/KEY: Oligonucleotide Primer DRB23
    ( B ) LOCATION: Anneals to codons 7 to 13 of the DRB1 transcript of HLA class II ( x i ) SEQUENCE DESCRIPTION: SEQ ID NO: 42:

```
        TTC TTG CAG CAG GAT AAG TA              20
        Phe Leu Gln Gln Asp Lys Tyr
                     10
```

( 2 ) INFORMATION FOR SEQ ID NO: 43:

( i ) SEQUENCE CHARACTERISTICS:
    ( A ) LENGTH: 21 base pairs
    ( B ) TYPE: Nucleic Acid
    ( C ) STRANDEDNESS: Single
    ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
    ( A ) NAME/KEY: Oligonucleotide Primer DRB24
    ( B ) LOCATION: Anneals to codons 5 to 11 of the DRB1 transcript of HLA class II ( x i ) SEQUENCE DESCRIPTION: SEQ ID NO: 43:

```
        CCA CGT TTC TTG GAG TAC TCT             21
        Pro Arg Phe Leu Gly Tyr Ser
         5                  10
```

( 2 ) INFORMATION FOR SEQ ID NO: 44:

( i ) SEQUENCE CHARACTERISTICS:
    ( A ) LENGTH: 21 base pairs
    ( B ) TYPE: Nucleic Acid
    ( C ) STRANDEDNESS: Single
    ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
    ( A ) NAME/KEY: Oligonucleotide Primer DRB25
    ( B ) LOCATION: Anneals to codons 6 to 13 of the DRB1 transcript of HLA class II ( x i ) SEQUENCE DESCRIPTION: SEQ ID NO: 44:

```
        T TTC TTG GAG CAG GTT AAA CA            21
        Arg Phe Leu Glu Gln Val Lys His
                         10
```

( 2 ) INFORMATION FOR SEQ ID NO: 45:

( i ) SEQUENCE CHARACTERISTICS:

(A) LENGTH: 21 base pairs
(B) TYPE: Nucleic Acid
(C) STRANDEDNESS: Single
(D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
(A) NAME/KEY: Oligonucleotide Primer DRB16
(B) LOCATION: Anneals to codons 29 to 35 of the
DRB1, DRB3, DRB4 and DRB5 transcripts of HLA
class II (xi) SEQUENCE DESCRIPTION: SEQ ID NO: 45:

```
AGA  TGC  ATC  TAT  AAC  CAA  GAG                    21
Arg  Cys  Ile  Tyr  Asn  Gln  Glu
     30                       35
```

(2) INFORMATION FOR SEQ ID NO: 46:

(i) SEQUENCE CHARACTERISTICS:
(A) LENGTH: 21 base pairs
(B) TYPE: Nucleic Acid
(C) STRANDEDNESS: Single
(D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
(A) NAME/KEY: Oligonucleotide Primer DRB17
(B) LOCATION: Anneals to codons 29 to 35 of the
DRB1, DRB3, DRB4 and DRB5 transcripts of HLA
class II (xi) SEQUENCE DESCRIPTION: SEQ ID NO: 46:

```
AGA  TAC  TTC  CAT  AAC  CAG  GAG                    21
Arg  Tyr  Phe  His  Asn  Gln  Glu
     30                       35
```

(2) INFORMATION FOR SEQ ID NO: 47:

(i) SEQUENCE CHARACTERISTICS:
(A) LENGTH: 21 base pairs
(B) TYPE: Nucleic Acid
(C) STRANDEDNESS: Single
(D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
(A) NAME/KEY: Oligonucleotide Primer DQB6
(B) LOCATION: Anneals to codons -8 to -2 of the
DQB1 transcript of HLA class II (xi) SEQUENCE DESCRIPTION: SEQ ID NO: 47:

```
CTG  AGC  ACC  CCA  GTG  GCT  GAG                    21
Leu  Ser  Thr  Pro  Val  Ala  Glu
```

(2) INFORMATION FOR SEQ ID NO: 48:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
        (A) NAME/KEY: Oligonucleotide Primer DQB14
        (B) LOCATION: Anneals to codons -8 to -2 of the
            DQB1 transcript of HLA class II (xi) SEQUENCE DESCRIPTION: SEQ ID NO: 48:

```
CTG  AGC  TCC  TCA  CTG  GCT  GAG           21
Leu  Ser  Ser  Ser  Leu  Ala  Glu
              -5
```

(2) INFORMATION FOR SEQ ID NO: 49:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
        (A) NAME/KEY: Oligonucleotide Primer DQB15
        (B) LOCATION: Anneals to codons -8 to -2 of the
            DQB1 transcript of HLA class II (xi) SEQUENCE DESCRIPTION: SEQ ID NO: 49:

```
CTG  AGC  ACC  TCG  GTG  GCT  GAG           21
Leu  Ser  Thr  Ser  Val  Ala  Glu
              -5
```

DNA SEQUENCE-BASED HLA TYPING METHOD

GOVERNMENT SUPPORT

This invention was made with Government support under grant number DK 36828 by the U.S. National Institutes of Health. The Government has certain rights in the invention.

TECHNICAL FIELD

The present invention relates to a process for determining genotypes of highly polymorphic systems, such as the major histocompatibility complex of humans, including Class I and Class II HLA genes. Specifically, the method of the present invention involves amplifying the alleles carried by any given individual at a gene locus or loci of interest by polymerase chain reaction with conserved and non-conserved oligonucleotide primers. The polymerase chain reaction products are directly sequenced followed by evaluation of the resulting nucleic acid ladders to determine the genotype of sample nucleic acid.

BACKGROUND OF THE INVENTION

The major histocompatibility complex (MHC) includes the human leukocyte antigens (HLA) gene complex which is located on the short arm of human chromosome six. This region encodes cell-surface proteins which regulate the cell-cell interactions of the immune response. The various HLA Class I loci encode the HLA antigens, 44,000 dalton polypeptides which associate with B-2 microglobulin at the cell surface. The Class I molecules are involved in the recognition of target cells by cytotoxic T lymphocytes. HLA Class II loci encode cell surface heterodimers, composed of proteins of 29,000 and 34,000 daltons, respectively. These Class II molecules are also involved in the recognition of target cells by helper T lymphocytes.

The HLA-A, HLA-B, and HLA-C loci of the HLA Class I region as well as the HLA-DRB, HLA-DQB, HLA-DQA, HLA-DPB and HLA-DPA loci of the HLA Class II region exhibit an extremely high degree of polymorphism. The WHO nomenclature committee for factors of the HLA system [Marsh and Bodmer, *Immunogenetics*, 31:131 (1990)] designated 25 alleles of HLA-A (HLA-A-0101, A-0201, etc.), 32 alleles of HLA-B, and 11 alleles of HLA-C, 43 HLA-DRB alleles, 13 HLA-DQB alleles, 8 HLA-DQA alleles, 4 HLA-DPA alleles and 19 HLA-DPB alleles. Since this high degree of polymorphism is thought to relate to the function of the HLA molecules, much effort has gone into determining its molecular basis and the functional implications of its polymorphisms (i.e., in transplantation). With the cloning of certain HLA genes this effort has extended to the DNA level.

The Class II genes of the HLA-D region on the short arm of human chromosome six constitute one of the most polymorphic genetic systems known [Bach, *Immunol. Today*, 6:89 (1985)]. The HLA Class II molecules (DR, DQ and DP) are heterodimeric glycoproteins composed of two non-covalently associated chains (alpha and beta) which serve as restricting elements in nominal antigen presentation in the context of self [Zinkernagel and Doherty, *Nature*, 248:701 (1974)] or as foreign antigens in alloresponses [Bach and Van Rood, *N. Engl. J. Med.*, 295:806 (1976)].

Allelic polymorphism of the HLA-D region encoded specificities can be determined by serological methods for phenotyping, mixed lymphocyte cultures using homozygous typing cells, primed lymphocyte testing, determination of restriction fragment length polymorphisms and, more recently, oligotyping [Bach, supra (1985); Bidwell, *Immunol. Today*, 9:18 (1988); Tiercy et al., *Proc. Natl. Acad. Sci. U.S.A.*, 85:198 (1988)]. Present efforts focus largely on the development of molecular approaches to typing, such as RFLP and oligotyping [Bidwell, supra (1988); Tiercy et al., supra (1988); Erlich and Bugawan, in *PCR Techniques*, H. A. Erlich, ed., Stockton Press, New York (1989)].

The cloning and sequencing of several HLA-DR, DQ, and -DP alleles has revealed that their amino acid polymorphisms are located in hypervariable regions of their N-terminal domains, encoded by the second exon of DRB1, DRB3/4/5, DQA1 and DQB1, DPA1 and DPB1 genes [Marsh and Bodmer, supra (1990); Todd et al., *Nature*, 329:599 (1987)]. This information has allowed the design of allele-specific oligonucleotides which can be used in the characterization of the known HLA Class II polymorphisms by means of their hybridization to DNA on a solid support (oligomer typing) or for sequencing [Tiercy et al., supra (1988); Erlich and Bugawan, supra, (1989); Todd et al., supra (1987); Saiki et al., *Science*, 230:1350 (1985); Mullis and Faloona, *Methods Enzymol.*, 155:335 (1987); Saiki et al., *Nature*, 324:163 (1986); Scharf et al., *Science*, 233:1076 (1986); Gyllenstein and Erlich, *Proc. Natl. Acad. Sci. U.S.A.*, 85:7652 (1988)]. Oligonucleotide typing, although rapid, requires the use of a rather large number of oligonucleotides for each locus and cannot detect previously unidentified sequence polymorphisms, likely to exist in non-Caucasian populations; further, the approach may not be easily applicable to and may not be practical for the analysis of Class I polymorphisms. Direct sequencing of single-stranded DNA generated by PCR using allele-specific oligonucleotides has been successfully used to examine polymorphism at DQA1 locus [Gyllenstein and Erlich, supra (1988)]. Application of this approach to DRB genes is, however, problematic due to the strong sequence homology among DRB1, DRB3, DRB4 and DRB5 genes and the presence of up to four different versions of each of these genes in most individuals (isotypic complexity). The very complex ladders generated by direct sequencing make this present process impractical for accurate and rapid determination of HLA types. Thus, direct sequencing of HLA-PCR products has been limited to previous knowledge of the HLA types carried by a given individual and as such is not suitable for routine HLA typing [Bach, supra (1985); Bidwell, supra (1988); Tiercy et al., supra (1988); Erlich and Bugawan, supra (1989)].

Currently, HLA typing is routinely done in connection with many medical procedures, e.g., organ transplantation. Rejection of organ grafts is believed to be diminished if the HLA alleles of donor and recipient are identical. The numerous alleles of HLA genes in the population also make HLA typing useful for paternity testing. However, the currently available techniques are incapable of differentiating among all of the polymorphisms associated with the alleles at Class I and Class II HLA loci. Other drawbacks to current HLA typing are the availability of standard sera necessary to conduct serological tests, the speed of obtaining test results (i.e., MLC takes 5–7 days), and that only the already known HLA types, but not new polymorphisms, are detected by these techniques. In the case of tissue typing in organ transplants and in relatively high volume genetic evaluations, such as paternity testing, the length of time associated with current HLA typing techniques-causes unnecessary delay and the results may not be highly accurate.

Accordingly, there is a need for a method to determine genomic information in highly polymorphic systems that addresses the limitations imposed by previous methods, that is, a system that is capable of determining the nucleotide sequences of the genes carried by any given individual without the need to have previous knowledge of his or her HLA types as defined by other methods. Furthermore, the invention avoids the use of oligonucleotides specific for each known allele. The technique we present is rapid, requires the use of only a small number of oligonucleotide primers, can readily detect new sequence variants unidentifiable with more conventional approaches, is applicable to the analysis of other Class II as well as Class I and Class III genes and is automatable.

SUMMARY OF THE INVENTION

The present invention relates to a method for determining the nucleic acid sequence of one or more polymorphic genes of a subject by amplifying and direct sequencing genomic or complementary DNA molecules for each allele at each gene locus to be sequenced using conserved and non-conserved (non-allele-specific) oligonucleotide primers. The method is specifically designed to provide rapid and accurate determination of a major histocompatibility complex class genotype of a subject in a sample (e.g., Class I or Class II). Most particularly, the method is directed to determining at least one HLA Class II gene locus including DRB1, DRB3, DRB4, DRB5, DQB1, DQA1, DPA1 and DPB1 genes. In the case of Class I genotypes, the method is envisioned as being useful to determine A, B, and C loci genes.

To determine a gene locus nucleic acid sequence polymorphism with the method of the present invention, nucleic acid (RNA or DNA) from a sample is isolated. In the case of RNA, cDNA molecules for each allele of at least one gene locus to be sequenced are synthesized by employing a locus-specific oligonucleotide primer that anneals to a conserved region of each allele of each gene locus. According to the present invention, the sample nucleic acid sequence is determined by: amplifying the cDNA molecules or genomic DNA by polymerase chain reaction to generate sufficient product for each allele of each gene locus to be sequenced, with all of the alleles for each gene locus and chromosome to be sequenced being amplified with at least one conserved oligonucleotide primer pair, and at least one of the alleles of each gene locus and chromosome to be sequenced being amplified with at least one non-conserved oligonucleotide primer and at least one conserved primer; preparing the products of each PCR for sequencing (clean); sequencing directly the products of each polymerase chain reaction product to detect each allele at each gene locus of each chromosome with Taq polymerase and a conserved primer specific for each locus that is sequenced; and analyzing each sequenced product for each locus and primer combination(s) to determine the genotype of the subject.

In a preferred embodiment of the present invention the sequence of each polymerase chain reaction product for each allele of each gene locus is determined by analyzing each nucleic acid single and/or overlapping ladder generated for each directly sequenced polymerase chain reaction product. The analysis is conducted by comparing the nucleotide sequence of each allele of each gene locus sequence to known sequences for each locus, followed by comparing the sequence of each gene locus amplified with the non-conserved/conserved oligonucleotide primer pair to the nucleotide sequence of each allele of the gene locus amplified with a conserved oligonucleotide primer pair. Comparison of nucleic acid ladders for sequenced alleles can be conducted visually or using computer software.

In a preferred embodiment, the process of the invention is automated for use in rapid genotype determinations, including diagnosis of genetic diseases. Automation of the process includes isolating the sample nucleic acid with an RNA/DNA extractor; amplifying the synthesized cDNA molecule or the isolated DNA molecule by polymerase chain reaction using a thermocycler to generate the polymerase chain reaction products; sequencing the polymerase chain reaction products in an automated sequencing apparatus; and analyzing each sequenced polymerase chain reaction product with the computer having a database with allelic sequence information and the capacity to conduct the appropriate substraction algorithm for comparing the polymerase chain reaction product sequence for each allele amplified with a conserved oligonucleotide primer pair to the nucleic acid sequence of each allele sequenced with a non-conserved/conserved oligonucleotide primer pair.

The invention further relates to specific groups of oligonucleotide primers useful in the steps of cDNA synthesis, cDNA/genomic DNA amplification by polymerase chain reaction and direct sequencing of the polymerase chain reaction products to determine the nucleotide sequence of each of the alleles at each locus of each chromosome that is amplified. Useful single strand DNA oligonucleotide primers are described in Table 1 herein.

BRIEF DESCRIPTION OF THE DRAWINGS

FIG. 1A shows a schematic of the cDNA/PCR/Sequencing experiments for DRB (DRB1, DRB3, DRB4 and DRB5), DQA1, DQB1, DPA1 and DPB1 genes.

FIG. 1B–1Fshows a schematic of the primer binding sites on DRB, DQA1, DQB1, DPA1 and DPB1 transcripts. Stippled boxes represent primers used in the cDNA synthesis reactions; black boxes represent conserved (or Type 1) primers, used for PCR; checked boxed represent non-conserved (or Type 2) primers, also used for PCR; and blank boxes represent sequencing primers.

DETAILED DESCRIPTION OF THE INVENTION

Figure 1G:
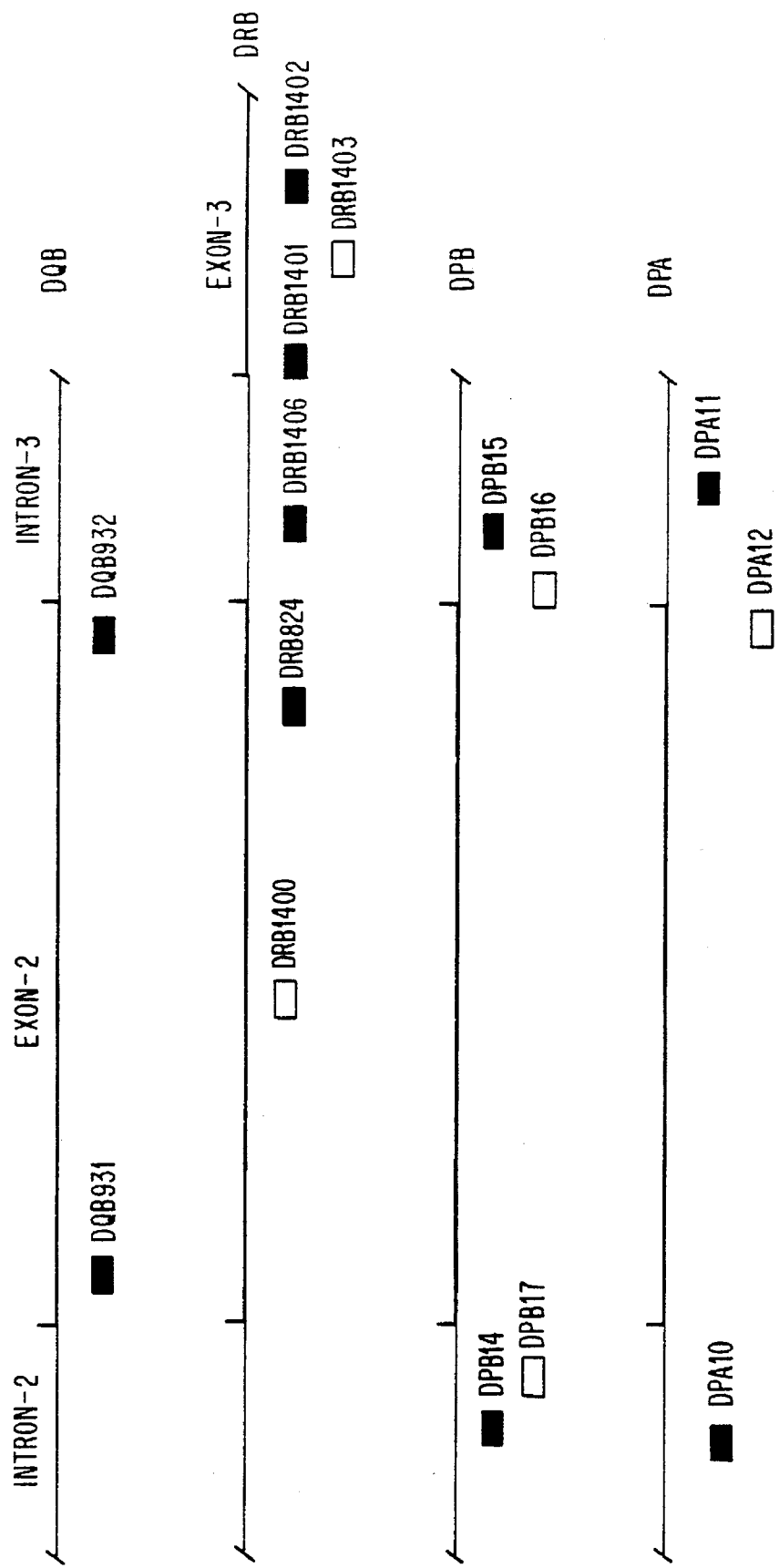
FIG. 1G shows a schematic of the primer binding sites on DQB1, DRB, DPB1 and DPA1 genes in their germline configuration. Only those primers exclusively used for genomic DNA samples are shown in the Figure. For Class II DNA typing, only the primers that are not shown in FIGS. 1B–1E are shown in this Figure. The combinations of primers used for performing the appropriate reactions are shown in Table II(2).

As used herein, the term "gene" refers to a segment of DNA, composed of a transcribed region and a regulatory sequence that makes possible a transcription. The term "gene locus" refers to the specific place on the chromosome where a gene is located. The term "allele" refers to the multiple forms of a gene that can exist at a single gene locus at a single chromosome and are distinguishable from the other possible alleles by their differing effects on phenotype (detectable outward manifestations of a specific genotype). "Haplotype" refers to the specific allele composition of the genes at multiple loci on the same chromosome. As used herein the term "genotype" refers to the specific allelic composition of a gene at multiple linked loci at each chromosome (2 haplotypes).

The term "oligonucleotide" as used herein refers to a molecule having two or more deoxyribonucleotides or ribonucleotides, preferably more than three deoxyribonucleotides. The exact number of nucleotides in the molecule will depend on the function of the specific oligonucleotide molecule. As used herein the term "primer" refers to a single stranded DNA oligonucleotide sequence, preferably produced synthetically which is capable of acting as a point of initiation for synthesis of a primer extension product which is complementary to a nucleic acid strand to be copied or a point of initiation for sequencing a DNA molecule. In the case of primers intended for use in synthesizing cDNA or amplifying cDNA or genomic DNA molecules by polymerase chain reaction products, the length and sequence of the primer must be sufficient to prime the synthesis of extension products in the presence of a polymerization enzyme. Preferably, the length of the primer is from about 5–50 nucleotides, more preferably from about 5–20 nucleotides. Specific length and sequence of the primer will depend on complexity of required DNA or RNA target templates, as well as conditions of primer employment such as temperature, ionic strength, and $MgCl_2$ concentration. When nested primers are used for sequencing, the number of base pairs separating the amplification and sequencing primers on the DNA template are also important considerations.

As used herein, "conserved oligonucleotide primer" (Type 1) refers to an oligonucleotide molecule that corresponds to a region of high DNA sequence conservation (i.e. less than 1–2 nucleotide variations). While the conserved primer need not correspond exactly to the nucleotide template to which it anneals, the conserved primer will have minimal, preferably less than one mismatch with the target nucleotide template. Functionally, conserved primers are capable of equally priming the target nucleotide (cDNA, PCR product, etc.) at high stringency conditions. In contrast to this, as used herein, "non-conserved oligonucleotide primer" (Type 2) refers to an oligonucleotide molecule that has an intended number of mismatches with the possible target nucleotide sequences. The intended number of mismatches can vary with a preferred number of mismatches being about 1–12. Non-conserved primers are characterized by their selective binding to a limited number of alleles at a given locus or at a group of highly homologous loci. The non-conserved primer will bind to the more complementary allele or group of alleles (two or less than two) (i.e., fewer number of mismatches between primer and target template sequence). The specific combinations of conserved and non-conserved primers and the number of reactions per locus or loci used herein are specifically designed to obtain highly accurate results with minimal expenditure of time and cost.

The present invention is directed to a process for determining the sequences of the alleles of highly polymorphic gene systems carried by any given individual, such as, for example, the human HLA system, most particularly Class II and Class I genes, using enzymatic amplification and direct sequencing of the gene cDNA molecules using a limited number of primers and avoiding the use of allele specific oligonucleotides as much as possible. The present method is particularly well suited to determining allelic sequences of Class II HLA genes, thereby providing complete HLA Class II genotype information for a subject. Using the method of the present invention complete Class II HLA typing (DR, DQ and DP) can be performed in about 16 to 24 hours or less.

Generally, the method of the present invention involves: extraction of sample nucleic acid; in the case of RNA, generation of cDNA; cDNA or genomic DNA amplification; direct sequencing of amplification products; and analysis of the direct sequence information. Generation of cDNA, amplifying the cDNA and direct sequencing the cDNA amplification products is accomplished using oligonucleotide primers with specific characteristics, such as those described herein.

A. Oligonucleotide Primers

The oligonucleotide primers of the present invention can be synthesized using any known suitable method, such as phosphotriester and phosphodiester methods. Narang et al., *Methods Enzymol.*, 68:90 (1979); Brown et al., *Methods Enzymol.*, 68:109 (1979). Oligonucleotides can be prepared using a modified solid support such as a Biosearch 8750 DNA synthesizer. Useful primers can also be isolated from a biological source using appropriate restriction endonucleases which cut double stranded DNA at or near a nucleotide sequence of interest for use as a primer.

B. Extraction of Sample Nucleic Acid

In the process of the present invention any source of nucleic acid can be used as the sample nucleic acid, as long as the sample contains the nucleic acid sequence of interest. For example, the sample chosen for the present method can be RNA, DNA or a DNA/RNA hybrid. While typical samples include peripheral blood mononuclear cells, (PBMNC's), lymphoblastoid cell lines (LCL's), hair cells or the like, for determining human HLA Class II and Class I gene polymorphisms LCL's or PBMNC's are preferred. The nucleic acid to be isolated (e.g. RNA or DNA) will depend on the source of genetic material (blood stain, hair, or peripheral blood cells). However, in the case of HLA Class II genes including DRB1–5, DQB1, DQA1, DPA1, DPB1 the preferred isolated nucleic acid is total cellular RNA when the typing is to be done for transplantation purposes or paternity testing. For forensic uses, genomic DNA may be the preferred genetic material in which case different primer considerations would be used. Cytoplasmic and poly(A)+ RNA can also be used. It is envisioned that isolation of sample nucleic acid for the present process can be automated using a DNA/RNA extractor (such as Model 341 DNA extractor available from Applied Biosystems, Inc.; Foster City, Calif.).

C. Generation of cDNA

Complementary DNA (cDNA) of the sample nucleic acid is generated using specific oligonucleotide primers and cloned reverse transcriptase following general conditions suggested by the enzyme manufacturer (Bethesda Research Laboratories, Gaithersburg, Md.). Specific differences in type and amount of primers used, dNTP concentrations and elongation times will be readily apparent to those of skill in the art based on the Examples that follow.

D. Polymerase Chain Reaction

Amplification of cDNA or genomic DNA for each gene locus of interest is accomplished using the polymerase chain reaction (PCR) as generally described in U.S. Pat. Nos. 4,683,195 and 4,683,202 to Mullis. The PCR consists of many repetitions of a cycle which consists of: (a) a denaturation step, which melts both strands of a DNA molecule; (b) an annealing step, which is aimed at allowing the primers to anneal specifically to the melted strands of the DNA molecule; and (c) an extension step, which incorporates to the primers deoxyribonucleotides complementary to those of the strand of DNA to which the primers are annealed. The PCR process, as indicated in the Examples, can be conducted using a Thermocycler (Perkin-Elmer, Cetus, Emeryville, Calif.).

The present invention introduces the use of non-conserved oligoprimers in the PCR procedure specifically designed to solve the problems one would face in performing HLA typing by sequencing DNA amplified exclusively by using conserved primers or allele specific oligonucleotides (see below). It is understood that the PCR process is designed for the amplification of specific genes with the use of oligonucleotides specific for the particular gene to be amplified. However, even using completely matched primers, in most cases the PCR is not absolutely specific. For HLA-DRB genes and Class I genes, the use of conserved primers in PCR will generate complex mixtures of templates, which upon direct sequencing will be seen as overlapping sequencing ladders, cumbersome to interpret. Therefore, genes for which the exact nucleotide sequence information is unknown can not be achieved with an adequate level of certainty. Use of non-conserved oligonucleotides which can selectively anneal under high stringency conditions to two or fewer alleles of a gene locus or group of homologous loci can provide sequence information for the different genes at highly homologous loci in complex heterozygote combinations. This is of particular importance to HLA typing, and is applicable to Class I HLA typing as well as Class II typing. The difference between non-conserved primers and allele-specific oligonucleotides resides in that the latter can only be used when the presence of a particular allele is known, and also requires the use of a specific primer for each of the alleles of the polymorphic system. Thus, combining use of a non-conserved primer and conserved primers to amplify the separate alleles of highly homologous polymorphic gene loci can provide simpler DNA polymerase chain reaction product combinations sufficient to allow unambiguous interpretation of direct sequencing ladders of each allele for genotype determinations with moderate expenditure of time and economical cost.

The conditions used for the PCR reactions are preferably the same except for the temperature used in the annealing step, which is different depending on the type of primer used, conserved (Type 1) or non-conserved (Type 2). Reactions that use the former primer type are preferably performed at 37° C. in the annealing step of the cycle, whereas this step is preferably performed at about 55° C. to 0° C. in reactions that use the later type of primers. The concentrations of primers, and buffers used will be apparent from and include the process parameters described in the Examples that follow.

E. Direct Sequencing of PCR Products

Direct sequencing of double-stranded DNA generated by the PCR is accomplished using Taq polymerase and specific combinations of reagents at appropriate concentrations. The sequencing procedure can be conducted in an automatic sequencing apparatus such as the 373A Model DNA Sequencer from Applied Biosystems Inc. (Foster City, Calif.). The reagents, including sequencing primers and nucleic acid termination mixtures will be understood by those of skill in the art based on the direct sequencing procedure specified in the following Examples.

F. Analysis of Direct Sequenced PCR Products

The nucleic acid ladders resulting from direct sequencing the cDNA or genomic DNA for each gene locus of interest can be assessed visually from autoradiograms or by employing a computer programmed with nucleotides sequence information for all alleles of all haplotypes and procedures for comparing sequenced alleles and known alleles of gene loci of interest. In a preferred embodiment of the present invention, the evaluation of gene locus alleles involves a two step process: (a) comparison of the gene sequences of each polymerase chain reaction product (i.e., conserved and non-conserved primer products) with a library of known genotype information such as the information obtained on homologous cell lines very well characterized by methods other than sequencing [Marsh and Bodmer, Immunogenetics, 31:131 (1990)] as well as sequences of individual alleles; followed by (b) comparison of direct sequence information for the polymerase chain reaction product of an allele of a gene locus amplified with a conserved oligonucleotide primer pair and polymerase chain reaction product of alleles of a gene locus or loci amplified with a conserved/non-conserved primer pair. This comparison employs a substitution algorithm or visual cancellation of duplicative sequence ladder information to generate the specific sequence information for each allele of a gene locus.

It is envisioned that the process of the present invention can be used to amplify and sequence known and unknown highly polymorphic systems (e.g., Class I and Class II HLA typing, and Class III typing). The method is particularly well suited for Class II HLA typing, reducing its costs, increasing its speed and especially improving its accuracy. The present process is believed to be useful for paternity testing and forensic medicine, with more accuracy than restriction fragment length polymorphism (RFLP), DNA fingerprinting or dot blot-detection systems. While in the latter only a hybridization pattern is observed, direct sequencing of amplified products shows the exact nucleotide sequence of the amplified genes, and hence is more accurate and reliable.

As evidenced by the following Examples, sequence polymorphism analysis of DRB1, DRB3, DRB4, DRB5, DQB1, DQA1, DPA1 and DPB1 genes can be rapidly performed in any subject of unknown HLA type by means of enzymatic amplification and direct sequencing of Class II genes using a limited number of conserved and non-conserved oligonucleotides. The approach described herein is entirely automatable using currently available technology and, as opposed to previously described methods using oligonucleotide probes and dot blots, has the advantage of detecting the presence of new allelic sequences or sequence microheterogeneity at the population level. The methodology of the present invention is envisioned to be useful for detailed analyses of the effects of sequence allelism at different Class II HLA loci on graft survival after allogeneic transplantation. The method of the present invention allows rapid and precise sequence analysis of Class II HLA polymorphism in studies of human disease and may be of interest in the search for new Class II sequence variants in large populations of subjects.

The present invention is further described by illustration in the following Examples which are not intended to limit the invention.

EXAMPLE I

1. Preparation of Oligodeoxyribonucleotide Primers and Sequence Primer Combinations Useful for cDNA/PCR/Sequencing Reactions of Class II HLA Genes All of the oligodeoxyribonucleotide primers described herewithin were synthesized as described below:

Automated Synthesis of oligodeoxyribonucleotide primers: The b-cyanoethylphosphoamidites, obtained from Milligen-Biosearch (Novato, Calif.), were sequentially condensed to a nucleoside derivatized controlled pore glass >support using a Biosearch 8750 DNA synthesizer. Condensation cycles included detritylation with dichloroacetic acid in dichloromethane, followed by condensation with benzotriazole and capping with acetic anhydride and 1-methylimidazole in tetrahydrofuran and pyridine, with each cycle time being approximately 9 minutes. Yields at each step were 99% as determined by measuring dimethoxytrityle alcohol release. The methodology for oligodeoxyribonucleotide synthesis is described in Caruthers, et al., *Methods Enzymol.*, 154:287 (1987).

Deprotection and purification of oligodeoxyribonucleotide primers: Deprotection and purification of oligodeoxyribonucleotide primers was performed using the procedure described by Schulhof et al., *Nucl. Acids Res.*, 15:397 (1987). Briefly, the oligodeoxyribonucleotide was removed from the solid support by exposure to concentrated ammonium hydroxide at room temperature for about one hour. The solution containing the partially deprotected oligodeoxyribonucleotide was brought to 65° C. for 16 hours. Ammonia was removed and the residue was subjected to chromatography on a C18 reverse-phase column (RP 304, BioRad, Richmond, Va.) using a linear gradient of 14 to 20% acetonitrile in 0.1 molar ammonium/triethylamine, pH 7.0. The dimethoxytrityl group was removed from the HPLC-purified oligodeoxyribonucleotide by treatment with 70% acetic acid. The detritylated oligodeoxyribonucleotide was recovered by precipitation in ether, vacuum centrifuged until dry, resuspended in water and quantitated by measuring its absorbance at 260 nm.

Using the above procedure, the following oligonucleotide primers corresponding to specified regions of HLA Class II DQA, DQB, DRB, DPB and DPA loci were synthesized (see Table I below) and extensively tested:

TABLE I

Oligonucleotides Used For The cDNA/PCR/Sequencing Reactions

| Sequence Listing No. | (Seq.) Type 1 | | Anneal | Locus(i) | Template | Step |
|---|---|---|---|---|---|---|
| 1 | DQB7 | 5'-GGT GGT TGA GGG GCC TCT GTC C-3' | 105–111 | DQB1 | RNA | RT/PCR |
| 2 | DRB20 | 5'-GT GCT GCA GGG GCT GGG TCT T-3' | 105–111 | DRB1/3/4/5 | RNA | RT/PCR |
| 3 | DQA9 | 5'-GGT GAG GTT ACT GAT CTT GAAG-3' | 148–155 | DQA1 | RNA | RT/PCR |
| 4 | DQB13 | 5'-AGA GAC TCT CCC GAG GAT TT C-3' | 1–7 | DQB1 | RNA | PCR/SEQ |
| 5 | DRB22 | 5'-CT GGC TTT GGC TGG GGA CAC C-3' | −4/−3 | DRB1/3/4/5 | RNA/DNA | PCR/SEQ |
| 6 | DRB11 | 5'-TGT TCT CCA GCA TGG TGT GT C-3' | −33/−26 | DRB1/3/4/5 | RNA | PCR |
| 7 | DQA10 | 5'-CTG T CCT CCG TGA T GAG CCC-3' | −10/−4 | DQA1 | RNA | PCR |
| 8 | DQB932 | 5'-T CGC CT CTG CAG GGT CGC GCG-3' | 88–94 | DQB1 | DNA | PCR |
| 9 | DQB931 | 5'-TTT AAG GGC AT GT GCT ACT T C-3' | 11–17 | DQB1 | DNA | PCR |
| 10 | DQB30 | 5'-AT GGG GAG AT GGT CAC TGT GG-3' | 97–104 | DQB1 | RNA | SEQ |
| 11 | DRB30 | 5'-AGG AT ACA CAG T CAC CTT AGG-3' | 97–103 | DRB1/3/4/5 | RNA | SEQ |
| 12 | DQB5 | 5'-GT AGT TGT GT CT GCA CAC-3' | 78–83 | DQB1 | RNA/DNA | SEQ |
| 13 | DRB12 | 5'-GCC GCT GCA CT GT GAA GCT C-3' | 87–94 | DRB1/3/4/5 | RNA | SEQ |
| 14 | DQA29 | 5'-CAC GGT T CCG GT AGC AGC GGT AG-3' | 82–89 | DQA1 | RNA | SEQ |
| 15 | DQA30 | 5'-T ACG GT CCC T CT GGC CAG-3' | 19–24 | DQA1 | RNA | SEQ |
| 16 | DRB1400 | 5'-GCG CTT CGA CAG CGA CGT GG-3' | 38–45 | DRB1/3/4/5 | RNA/DNA | SEQ |
| 17 | DRB1401 | 5'-GAG GT GAC TGT GT AT CCT GAC-3' | 98–104 | DRB1*0701-2 | RNA/DNA | PCR |
| 18 | DRB1402 | 5'-GAT CAG GCC TGT GGA CAC CAC-3' | 142–148 | DRB1/3/4/5 | RNA/DNA | PCR |
| 19 | DRB1403 | 5'-CCG GAA CCA CCT GAC TT CAAT-3' | 127–133 | DRB1/3/4/5 | RNA/DNA | SEQ |
| 20 | DRB1406 | 5'-GCC AAG AGT GGG CCT CGC AGC-3' | bp18-38- intron 3 | DRB1/3/4/5 | DNA | PCR |
| 21 | DRB825 | 5'-AAC CCC GT AGT T GT GT CT GCA-3' | 79–85 | DRB1/3/4/5 | DNA | SEQ |
| 22 | DRB824 | 5'-GGG GAC ACC CGA CCA CGT TT C-3' | 1–7 | DRB1/3/4/5 | DNA | PCR |
| 23 | DPB10 | 5'-CGG ACA GT GGC T CT GAC GGC G-3' | −19/−13 | DPB1 | RNA | PCR |
| 24 | DPB11 | 5'-GTT GT GGT GCT GCA AGG GCC C-3' | 105–111 | DPB1 | RNA | RT/PCR |
| 25 | DPB12 | 5'-CTT GGA GGG GGA AAC ATT CAC-3' | 97–103 | DPB1 | RNA | SEQ/RT |
| 26 | DPB13 | 5'-T CT GT GGT CCA GGG CAG GGC C-3' | −5/2 | DPB1 | RNA | SEQ |
| 27 | DPB14 | 5'-AGA GGG AGA AAG AGG ATT AGA-3' | bp−42/−62 intron 2 | DPB1 | DNA | PCR |
| 28 | DPB15 | 5'-GCC CT GGG CAC GGG CCC GCG G-3' | bp 39/59 intron 3 | DPB1 | DNA | PCR |
| 29 | DPB16 | 5'-CGG CCC AAA GCC CT C ACT CAC-3' | bp 1–21 intron 3 | DPB1 | DNA | SEQ |
| 30 | DPB17 | 5'-CGC T CAT GT CCG CCC CCT CCC-3' | bp −6/−26 intron 2 | DPB1 | DNA | SEQ |
| 31 | DPA14 | 5'-GT CAAT GT GGC AGA T GAG GGT-3' | 104–110 | DPA1 | RNA | RT/PCR |
| 32 | DPA15 | 5'-CAT AT CAG AGC T GT GAT CTT G-3' | −17/−23 | DPA1 | RNA | PCR |
| 33 | DPA16 | 5'-CTT GGG AAA CAC GGT CAC CT C-3' | 88–94 | DPA1 | RNA | SEQ |
| 34 | DPA17 | 5'-CT GCT GAGT CT CCG AGG AGC T-3' | −3/−9 | DPA1 | RNA | SEQ |
| 35 | DPA10 | 5'-CT CT AGC TTT GAC CAC TT GC-3' | bp −69 to −50 intron 2 | DPA1 | DNA | PCR |
| 36 | DPA11 | 5'-AGT CT GAG GGT GGC AGA GAGG-3' | bp 55–71 intron 3 | DPA1 | DNA | PCR |
| 37 | DPA12 | 5'-GGC CT GAGT GT GGT TGG AAC G-3' | 76–82 | DPA1 | DNA/RNA | SEQ |
| 38 | DPA18 | 5'-CT GGC T AAC ATT GCT AT ATT G-3' | 59–65 | DPA1 | RNA | PCR |
| 39 | DPA19 | 5'-GGT CCC CT GGG CCC GGG GGT C-3' | 222–228 | DPA1 | RNA | RT |
| 40 | DPA20 | 5'-GCC AGA ACG CAG AGA CTT T AT-3' | 214–220 | DPA1 | RNA | SEQ |
| 41 | DPA21 | 5'-AAC TT GAAT ACC TT GAT CCA G-3' | 68–74 | DPA1 | RNA | SEQ |
| 42 | DRB23 | 5'-TT CTT GCA GCA GGAT AAGT A-3' | 7–13 | DRB1 | RNA/DNA | PCR |
| 43 | DRB24 | 5'-CCA CGT TT CTT GGA GT ACT CT-3' | 5–11 | DRB1 | RNA/DNA | PCR |
| 44 | DRB25 | 5'-TTT CTT GGA GCA GGT T AAA CA-3' | 6–13 | DRB1 | RNA/DNA | PCR |
| 45 | DRB16 | 5'-AGAT GCAT CT AT AAC CAA GAG-3' | 29–35 | DRB1/3/4/5 | RNA/DNA | PCR |
| 46 | DRB17 | 5'-AGAT ACTT CCAT AAC CAG GAG-3' | 29–35 | DRB1/3/4/5 | RNA/DNA | PCR |
| 47 | *DQB6 | 5'-CT GAG CAC CCC AGT GGC T GAG-3' | −8/−2 | DQB1 | RNA | PCR |

TABLE I-continued

Oligonucleotides Used For The cDNA/PCR/Sequencing Reactions

| Sequence Listing No. | (Seq.) Type 1 | | Anneal | Locus(i) | Template | Step |
|---|---|---|---|---|---|---|
| 48 | *DQB14 | 5'-CTGAGCTCCTCACTGGCTGAG-3' | −8/−2 | DQB1 | RNA | PCR |
| 49 | *DQB15 | 5'-CTGAGCACCTCGGTGGCTGAG-3' | −8/−2 | DQB1 | RNA | PCR |

All the above Type 1 primers are annealed at 37° C. and the Type 2 primers are annealed at 55° C. When the latter anneal at 37° C. in the PCR, they do not distinguish among allelic transcripts differing by few base pairs. This list of primers includes primers which are only used in certain situations, such as to confirm homozygosity at a particular locus whenever not expected according to the typings performed at the other linked loci. The alternative combinations of primers used in each step are described in Table II below. [(*) These primers anneal to a polymorphic region of DQB1 cDNAs (codons −8 to −2) encoding the 3' end of the signal peptide which has specific nucleotide nucleotide sequences for different DQB1 alleles (DQB6-DQB1*0601 and DQB1*0604-, DQB14-DQB1*0501-, DQB15- DQB1*0301-).] RT = Reverse transcription; SEQ = sequencing.

2. Combinations of Primers for cDNA/PCR/Sequence Reactions

There are specific combinations of oligonucleotide primers for each reaction and for each locus, including cDNA synthesis, PCR amplification and direct sequencing, which are designed to provide all the necessary sequence information for obtaining highly accurate, fast and inexpensive typing results. These combinations are listed in Table II below as "routine" combinations. In addition, Table II includes a list of "alternative" combinations of oligonucleotides for each locus which may be used to confirm results obtained with the "routine" combinations for a particular locus not expected according to, for instance, known haplotypic maps. These "unexpected" results are usually indicative of the existence of new alleles and/or haplotypes, which can be confirmed with the use of the alternative combinations of oligonucleotides. In any case, each of these combinations of oligonucleotides is characterized by its ability to generate an end-product (sequencing ladder) which is suitable of being accurately read by the naked eye or processed by computer operated under appropriate software.

For typing purposes in the clinical setting, such as in transplantation, the method uses RNA isolated from peripheral blood mononuclear cells as starting material; for forensic purposes, however, DNA is often the only available template. Although for each template (RNA or DNA) different combinations of oligonucleotides are used (see Table II), the general strategy for typing, including the interpretation of the results is essentially the same. The specific combinations of primers for "routine" RNA and DNA analysis, respectively, are described below in more detail. The general overview of the HLA typing strategy is shown in FIGS. 1 and 2 and discussed further in Examples 2 and 3.

TABLE II

Combinations of Primers for cDNA/PCR/Seq Reactions

1. RNA

| | Type | cDNA | PCR | A.T. | Seq* |
|---|---|---|---|---|---|
| Routine | | | | | |
| A. | 1 | DRB20 | DRB11 | 37° C. | DRB30/DRB12/DRB22** |
| B. | 2 | DRB20 | DRB23 | 55° C. | DRB30/DRB12 |
| C. | 2 | DRB20 | DRB24 | 55° C. | DRB30/DRB12 |
| D. | 2 | DRB20 | DRB25 | 55° C. | DRB30/DRB12 |
| E. | 1 | DQB7 | DQB13 | 37° C. | DQB30/DQB5 |
| F. | 1 | DQA9 | DQA10 | 37° C. | DQA30/DQA29*** |
| G. | 1 | DPB11 | DPB10 | 37° C. | DPB12/DPB13 |
| H. | 1 | DPA14 | DPA15 | 37° C. | DPA16/DPA17 |
| I. | 1 | DPA19 | DPA18 | 37° C. | DPA20/DPA21**** |
| Alternative | | | | | |
| J. | 2 | DRB20 | DRB16 | 55° C. | DRB30/DRB12 |
| K. | 2 | DRB20 | DRB17 | 55° C. | DRB30/DRB12 |
| L. | 1 | DRB20 | DRB22 | 37° C. | DRB30/DRB12 |
| M. | 1 | DQB7 | DQB6 | 37° C. | DQB13 |
| N. | 2 | DQB7 | DQB6 | 55° C. | DQB30/DQB5 |
| O. | 2 | DQB7 | DQB14 | 55° C. | DQB30/DQB5 |
| P. | 2 | DQB7 | DQB15 | 55° C. | DQB30/DQB5 |
| Q. | 1 | DPB12 | DPB10 | 37° C. | DPB13 |
| R. | 1 | DPA16 | DPA15 | 37° C. | DPA17 |

2. DNA

| | Type | PCR1 | PCR2 | A.T. | Seq |
|---|---|---|---|---|---|
| Routine | | | | | |
| S. | 1 | DRB1406 | DRB22 | 37° C. | DRB12/DRB1400***** |
| T. | 2 | DRB1406 | DRB24 | 55° C. | DRB12/DRB1400 |

TABLE II-continued

Combinations of Primers for cDNA/PCR/Seq Reactions

| | | | | | |
|---|---|---|---|---|---|
| U. | 2 | DRB1406 | DRB25 | 55° C. | DRB12/DRB1400 |
| V. | 2 | DRB1406 | DRB23 | 55° C. | DRB12/DRB1400 |
| W. | 1 | DQB932 | DQB931 | 37° C. | DQB5 |
| X. | 1 | DPB14 | DPB15 | 37° C. | DPB16/DPB17 |
| Y. | 1 | DPA10 | DPA11 | 37° C. | DPA12 |
| Alternative | | | | | |
| Z. | 1 | DRB12 | DRB824 | 37° C. | DRB825 |
| AA. | 2 | DRB1401 | DRB1402 | 55° C. | DRB1403# |
| AB. | 2 | DRB1406 | DRB16 | 55° C. | DRB825/DRB12 |
| AC. | 2 | DRB1406 | DRB17 | 55° C. | DRB825/DRB12 |
| AD. | 1 | DPB14 | DPB16 | 37° C. | DPB17 |

*For sequencing DRB and DQB two alternative sequencing primers are indicated, both sequencing the positive strand of DNA.
**Primer DRB22 is used to sequence the negative strand whenever new allelic sequences are identified.
***Each DQA1 sequencing primer anneals to a different strand. Reaction L uses an alternative amplification primer (DRB 22 instead of DRB11) in hypothetical situations where homozygosity may not be expected according to the rest of the haplotype. Reaction M is used for sequencing the negative strand of DQB1 in situations where new allelic sequences are identified.
****Sequencing of the third exon is necessary to distinguish among certain DPA1 alleles.
*****Primer DRB1400 may be used in sequencing amplified DRB genes from genomic DNA to read the sequences immediately following the 3' amplification primer. Reaction Q, R, Z and AD are alternative combinations for confirming homozygosity at the corresponding loci which may not be expected according to the rest of the Class II haplotype.
This primer combination is used to distinguish between DRB1*0701 and DRB1*0702, which differ by a single base pair in their third exons.

EXAMPLE II

Protocol: HLA Class II "Typing" by Direct Sequencing of DRB, DQB, DQA, DPA and DPB Genes 1. Cell Lines and Subjects Lymphoblastoid cell lines (LCLs) representing each of the known Class II haplotypes defined at the 10th International Histocompatibility Workshop [Dupont, *Hum. Immunol.*, 26, 3 (1989)] were provided by Dr. Miriam Segall (University of Minnesota). Forty unrelated subjects who had been previously serologically typed for Class I and Class II antigens were also studied. The serological types of each of the subjects under study were not known to the investigator performing the sequence analysis at the time the analysis was performed. These subjects included both healthy and affected (insulin-dependent diabetes and autoimmune thyroid disease) individuals. The sequenced haplotypes, many in heterozygote combinations, included: DR7 (n=3), DRw17 (n=26), DR4 (n=16), DRw11 (n=8), DRw8 (n=4), DR1 (n=6), DRw15 (n=6), DRw16 (n=2), DRw13 (n=2), DRw14 (n=2), DR212 (n=3), DR5×6 (n=3). The cell lines and heterozygote combinations tested are shown in Table III. Since the complexity at DPA and DPB loci is similar to that of DQ genes, the primer combinations for DPA and DPB typing were optimized in a smaller group of homozygote and heterozygote subjects.

2. HLA-DRB, DQB and DQA Transcript Amplification Using Conserved and Non-Conserved Oligonucleotides Total cellular RNA was prepared from (1 μg) from 5–10× $10^6$ peripheral blood mononuclear cells (PBMNC) or lymphoblastoid cell lines (LCLs) by cesium chloride centrifugation [Chirgwin et al. *Biochemistry*, 18, 5249 (1979)]. Alternatively, total RNA from peripheral blood (2–10 ml) was partially purified using a much faster protocol [Gouuh, *Anal. Biochem.*, 173, 93 (1988)]. One microgram of total cellular RNA was reverse transcribed with Moloney leukemia virus reverse transcriptase (MLVRT) (200 u, Bethesda Research Laboratories) in 50 mM Tris HCl, pH 8.3, 75 mM KCl, 10 mM DTT, 3 mM MgCl2, in the presence of the ribonuclease inhibitor RNAs in (10 units, Promega), 75 μM each dNTP and 10 pmols of a specific non-sense primer (Table II) in a 20 ml final volume for 30–45 min at 37° C. Eight μl of 10×PCR buffer (500 mM KCl, 100 mM Tris-Cl, pH 8.3, 7.5–15 mM MgCl2, 0.1% gelatin) were added after the incubation period. A 5'-primer (20 pmols) (Type 1 or Type 2 primers, respectively, see Table II) plus 10 pmols of the non-sense primer and two units of Taq polymerase were also added and the final volume was adjusted to 100 μl with distilled water. The reaction mixture was subjected to 35 cycles of 30 sec at 94° C., 30 sec at 37° C. or 55° C. and 30 sec at 72° C. using a Perkin-Elmer Cetus Thermocycler [see Saiki et al., supra (1985); Mullis and Faloona, supra (1987); Saiki et al., supra (1986); Scharf et al., supra (1986)]. The primers used here, their corresponding sequences and the regions to which they anneal are shown in Table II. The reactions for each locus are usually performed in separate microfuge tubes. However, when using conserved primers, the cDNA and PCR reactions for all loci (DRB, DQA, DQB, DPA and DPB) can be successfully performed simultaneously in the same tube.

3. Direct Sequencing of Amplified Products with Taq Polymerase

The reaction mixture (100 μl) was freed of unincorporated dNTPs and excess of oligonucleotides by spin-dialysis using Centricon-100 (Amicon) or Ultrafree-100 (millipore) microconcentrators. One-half of the retentate (20 μl) was dried down and resuspended in 15 μl of 1×Taq sequencing buffer (50 mM Tris-HCl, pH 9, 10 mM MgCl2). Internal oligonucleotides were used for priming the sequencing of DQB, DRB, DQA, DPB and DPA genes, respectively (Table II). Primers for sequencing each strand are listed in Table II. Only one strand is routinely sequenced for typing; sequencing of the other strand is performed in cases where a new allelic sequence is suspected. Eighty to 100 ng of primer were end-labelled with 10 pmol of gamma-P32 labelled ATP (5000 Ci/mmol, 10 μCi/μL) and 5 units of T4 polynucleotide kinase (Promega Biotec) in a 10 μl final volume. Ten ng of primer (1 μl) were added to the sequencing mixture without extraction of unincorporated labelled ATP, boiled for 5 min., and then left at room temperature for 15 min. Eight units of recombinant Taq polymerase (USB) were added to the mixture. Four μl of the annealed primer/template mixture were later added to 4 μl of each of the stop nucleotide mixes: a) Term mix ddG: 15 microM each dGTP, dATP, dCTP, dTTP; 45 microM ddGTP; b) Term mix ddA: 15 microM each dGTP, dATP, dCTP, dTTP; 600 microM ddATP; c) Term mix ddT: 15 microM each dGTP, dATP, dCTP, dTTP; 1200 microM ddCTP; d) Term mix ddC: 15 microM each dGTP, dATP, dCTP, dTTP; 450 microM ddCTP. The reactions were allowed to proceed for two consecutive periods of 10 min. at 72°–74° C. After the second cycle, each reaction was chased with 2 μl of a 7.5 μM mixture of ATP, GTP, TTP, CTP, and allowed to proceed for 5 min. After spinning down, the reaction was stopped by adding 4 ml of 95% (vol/vol) formamide/20 mM EDTA, heated to 80° C. for 5 min. and loaded on a 0.4 mm thick 6% polyacrylamide/7M urea gel. Electrophoresis was performed at 2500 V for 2 hr, the gel fixed in 5% (vol/vol) glacial acetic acid/5% (v/v) methanol for 15 min, dried, and exposed to Kodak X-Omat film for 4 to 12 hours.

RESULTS

1. Sequence-Based Typing of DR and DQ Polymorphic Genes in Homozygous Typing Cells Homozygous lymphoblastoid cell lines (LCLs) from the panel of the 10th International Histocompatibility Workshop (Table III) were used as an initial test of the methodology. In total, these cell lines were representative of most of the known DR and DQ alleles at the time the analysis was conducted.

Total cellular RNA isolated from homozygous LCLs was reverse-transcribed and the resultant cDNAs amplified using conserved oligonucleotides specific for DRB1/DRB3/DRB4/DRB5 or DQB1 or DQA1 genes as described in the preceding protocol. The conserved or Type 1 oligonucleotide primers anneal to regions of conserved DNA sequences; these regions are identical among the known alleles at each locus and flank the second exon of Class II genes. These conserved primers, as opposed to non-conserved or Type 2 primers, are designed to amplify all known alleles at DRB, DQA1 and DQB1 loci and, thus, all possible combinations of these alleles in any given heterozygote. The Type 1 oligonucleotides did not cross-amplify templates at loci other than those specified by the oligonucleotides (i.e., the DQA1 primers did not amplify DRB or DQB1 transcripts and vice versa); as expected, the DRB primers also amplified any DRB3, DRB4 or DRB5 transcripts present in addition to DRB1. Sequencing of these amplified templates was performed using a Type 1 primer annealing to a conserved region of the cDNAs internal to the sequence recognized by the amplification primers. FIG. 1A shows the general strategy for the method (SBT) and FIG. 1B–1F shows the relative position of each of the oligonucleotides used for the cDNA, PCR and sequencing reactions on the mature DRB, DQA and DQB mRNA molecules. The sequences of these primers, the loci they are specific for, the specific positions (codons) to which they anneal and the reaction(s) they are used in are indicated in Table II where the specific combinations of primers that can be used for the cDNA/PCR/sequencing reactions for each locus are identified. As noted in the legend to Table II, some of the primer combinations shown represent alternatives which may be useful in confirming results for a particular locus which do not fit with the expected sequences usually found with the rest of the haplotype. Each cDNA/PCR reaction is usually performed in a separate tube. However, when using Type 1 primers, the cDNA/PCR reactions for all the loci (DRB, DQA, DQB, DPA and DPB) can be performed simultaneously in the same tube. The products of each locus are sequenced in separate tubes. Following the conditions described in the above protocol, the sequence ladders between the sequencing primer and the 5' amplification primer could be clearly read starting from 2 to 14 bases from the sequencing primer binding site. No anomalous amplification products or sequencing ladders were detectable upon direct sequence analysis of amplified DRB, DQB1 and DQA1 cDNAs from the 43 homozygous cell lines tested (Table IIIa). The specific alleles at each Class II HLA locus composing the haplotypes carried by each of these cell lines are shown in Table IIIb. The number of ladders generated for each cell line was always that expected according to the specificity of the amplification primers (one DQB1 and one DQA1 ladder for all cell lines, one DRB ladder for DR1 and DRw8 cell lines and two DRB ladders for haplotypes of the DRw52 and DRw53 supertypic groups). Thus, analysis of the homozygous typing cell lines showed that the Type 1 primers used for cDNA synthesis, PCR and sequencing reactions allowed for accurate amplification and sequencing of all the tested alleles at each of these loci.

TABLE IIIa

| | Cell Lines and Heterozygote Combinations Tested | | |
|---|---|---|---|
| Cell Line | Class II HLA Type | Subject | Class II HLA Types** |
| SA | DR1-Dw1 | S1 | DR1-Dw1/DRw17 |
| MZ070782 | DR1-Dw20 | S2 | DR1-Dw1/DR4-Dw4 |
| KAS011 | DRw16-Dw21 | S3 | DR1-Dw1/DRw8.1 |
| *CALOGERO | DRw16-Dw- | S4 | DRw15-Dw2/DRw17 |
| *WJR076 | DRw16-Dw21 | S5 | DRw15-Dw2/DR4-Dw4 |
| *DEM | DRw16-Dw21/DR4 | S6 | DRw16-Dw21/DRw17 |
| WT24 | DRw16-Dw21 | S7 | DR5x6@/DRw17 |
| RML | DRw16-Dw22 | S8 | *DRw13-Dw18/DRw17 |
| SCHU | DRw15-Dw2 | S9 | DRw13-Dw19/DRw17 |
| WT8 | DRw15-Dw2 | S10 | DR4-Dw4/DRw17 |
| *AMAI | DRw15-Dw2 | S11 | DR4-Dw4/DRw12 |
| E4181324 | DRw15-Dw12 | S12 | DR4-Dw13/DR1-Dw1 |
| MT14B | DR4-Dw14 | S13 | DR4-Dw13/DRw17 |
| EJ32B | Drw17-SYD3 | S14 | DR4-Dw14/DRw15-Dw2 |
| RSH | DRw18-DwRSH | S15 | *DR4-Dw15/DRw17 |
| DEU | DR4-Dw4 | S16 | DRw11-Dw5/DRw17 |
| WT51 | DR4-Dw4 | S17 | DRw12/DR1-Dw1 |
| JBAF | DR4-Dw13 | S18 | DRw12/DRw8.1 |

TABLE IIIa-continued

Cell Lines and Heterozygote Combinations Tested

| Cell Line | Class II HLA Type | Subject | Class II HLA Types** |
|---|---|---|---|
| YAR | DR4-Dw10 | S19 | *DRw14-Dw9/DRw17 |
| KT17 | DR4-DKT2 | S20 | DR7/DRw17 |
| SPOO10 | DRw11-DB2 | S21 | DR4-Dw4/DR7 |
| JBUSH | DRw11-Dw5 | S22 | DRw8.1/DR7 |
| TISI | DRw11-DwTISI | S23 | Drw8.1/DR5x6@ |
| JVM | DRw11-DwJVM | S24 | DRw8.2/DRw11-Dw5 |
| BM16 | DRw12-DB6 | S25 | DRw8.3/DR1-Dw1 |
| *H0301 | DRw13-Dw19 | S26 | DRw8.3/DRw15-Dw2 |
| WDV | DRw13-Dw18 | S27 | DR9/DR1-Dw1 |
| WT47 | DRw13-Dw19 | | |
| TEM | DRw14-Dw9 | | |
| EK | DRw14-Dw9 | | |
| AMALA | DRw14-Dw16 | | |
| LBF | DR7-DB1 | | |
| BH | DR7-DB1 | | |
| CF96 | DR7-Dw7 | | |
| BER | DR7-Dw7 | | |
| DBB | DR7-Dw11 | | |
| MOU | DR7-Dw17 | | |
| BTB | Drw8-Dw8.1 | | |
| OLGA | DRw8-Dw8.2 | | |
| LUY | DRw8-Dw8.3 | | |
| TAB089 | DRw8-Dw8.3 | | |
| DKB | DR9-Dw23 | | |

The allelic composition at DRB, DQA1 and DQB1 loci for the sequenced haplotypes corresponded to that expected according to published sequence information from well characterized homozygous cell lines unless indicated (*).
*Haplotypes carrying new allelic sequences (DRB1, DRB3, DQA1 or DQB1 loci).
*Only the tested heterozygote comdinations are listed. The remainder of the 40 subjects tested were homozygotes or carried the ahplotypes listed in this table.
@This DRB specificity (DR5x6) has been given this arbitrary designation according to serological, RFLP and sequence information.

TABLE IIIB

Allelic Composition of Human Class II Haplotypes

| Haplotype | WS# | DRB1 | DRB3 | DRB4 | DRB5 | DQB1 | DQA1 |
|---|---|---|---|---|---|---|---|
| DR1-Dw1 | 9001 | *0101 | — | — | — | *0501 | *0101 |
| #DR1-Dw20 | 9002 | *0102 | — | — | — | *0501@ | *0101 |
| DRw16-Dw21 | 9009,-84,-15 | *1601 | — | — | *0201 | *0502 | *0102 |
| #DRw16-Dw21 | 9012,9007 | *1601 | — | — | *0202 | *0502 | *0102 |
| DRw16-Dw22 | 9016 | *1602 | — | — | *0202 | *0301 | *0501 |
| DRw15-Dw2 | 9013,9017 | *1501 | — | — | *0101 | *0602 | *0102 |
| #DRw15-Dw2 | 9010 | *1501 | — | — | -1.3 | *0602 | *0102 |
| DRw15-Dw12 | 9011 | *1502 | — | — | *0102 | *0601 | *0103 |
| DRw17-Dw3 | 9088 | *0301 | *0101 | — | — | *0201 | *1501 |
| DRw17-DwSYD | 9085 | *0301 | *0201 | — | — | *0201 | *0501 |
| DRw18-DwRSH | 9021 | *0302 | *0101 | — | — | *0402 | *0401 |
| DR4-Dw4 | 9025 | *0401 | — | *0101 | — | *0301 | *0301 |
| DR4-Dw4 | 9029 | *0401 | — | *0101 | — | *0302 | *0301 |
| DR4-Dw13 | 9030 | *0403 | — | *0101 | — | *0301 | *0301 |
| DR4-DKT2 | 9024 | *0403/6 | — | *0101 | — | *0302 | *0301 |
| DR4-Dw10 | 9026 | *0402 | — | *0101 | — | *0302 | *0301 |
| DR4-Dw14 | 9028 | *0404 | — | *0101 | — | *0302 | *0301 |
| DR4-Dw15 KT3 (a) | | *0405 | — | *0101 | — | *0401 | *0301 |
| # — | CC | *0405 | — | *0101 | — | *0201 | *0301 |
| DRw11-DB2 | 9036 | *1104 | *0201 | — | — | *0502 | *0102 |
| DRw11-Dw5 | 9035 | *1101 | *0201 | — | — | *0301 | *0501 |
| DRw11-Dwn | 9042 | *1103 | *0201 | — | — | *0301 | *0501 |
| DRw11-DwJVM | 9039 | *1102 | *0201 | — | — | *0301 | *0501 |
| DRw12-DB6 | 9038 | *1201 | *0201 | — | — | *0301 | *0501 |
| # — | 5x6 | DR5x6 | *0101 | — | — | *0301 | *0501 |
| #DRw13-Dw19 | 9055 | *1302 | *0301 | — | — | DQB6.5 | *0102 |
| DRw13-Dw18 | 9062 | *1301 | *0101 | — | — | *0603 | *0103 |
| DRw13-Dw18 (b) | | *1301 | *0101 | — | — | *0502 | *0102 |
| DRw13-Dw19 | 9063 | *1302 | *0301 | — | — | *0604 | *0102 |
| DRw14-Dw9 | 9057,9054 | *1401 | *0201 | — | — | *0503 | DQA1.4 |
| # — | MA | *1401 | *0201 | — | — | DQB5.4 | ND |
| DRw14-Dw16 | 9064 | *1402 | *0101 | — | — | *0301 | *0501 |
| DR7-DB1 | 9096,9046 | *0701 | — | *0101 | — | *0201 | *0201 |
| DR7-Dw7 | 9094,9093 | *0701 | — | *0101 | — | *0201 | *0201 |

TABLE IIIB-continued

| Allelic Composition of Human Class II Haplotypes | | | | | | | |
|---|---|---|---|---|---|---|---|
| Haplotype | WS# | DRB1 | DRB3 | DRB4 | DRB5 | DQB1 | DQA1 |
| DR7-Dw11 | 9052 | *0701 | — | *0101& | — | *0303 | *0201 |
| DR7-Dw17 | 9050 | *0701 | — | *0101 | — | *0201 | *0201 |
| DRw8-DW8.1 | 9067 | *0801 | — | — | — | *0402 | *0401 |
| DRw8-DW8.2 | 9071 | *0802 | — | — | — | *0402 | *0401 |
| DRw8-Dw8.3 | 9070 | *0803 | — | — | — | *0301 | *0601 |
| DRw8-Dw8.3 | 9066 | *0803 | — | — | — | *0601 | *0103 |
| DR9-Dw23 | 9075 | *0901 | — | *0101 | — | *0303 | *0301 |
| DRw10 (c–e) | | *1001 | — | — | — | *0501 | *0101 |

@, the DQB gene of the DR1-Dw20 haplotype differs from that of the DR1-Dw1 haplotype by a silent nucleotide substitution at codon 68.
# indicates the new haplotypes presented in this report.
&, This cell line does not translate its DRB4 mRNA (Knowles, 1989).
ND, not determined.
(a) Gregersen et al. 1986;
(b) Kao et al. 1989;
(c) Merryman et al. 1988;
(d) Todd et al. 1987;
(e) Merryman et al. 1989.

2. Amplification and Direct Sequencing of DQA1 and DQB1 cDNAs in Subjects of Unknown HLA Type DNA sequences have been determined for most HLA Class II allelic specificities defined by conventional HLA typing techniques (March, S. G. E., Bodmer, J. G. HLA-DRB nucleotide sequences, 1990. *Immunogenetics* 31:141, 1990; Todd, J. A., Bell, J. I., McDefvitt, H. O.: HLA-DQB gene contributes to susceptibility and resistance to insulin-dependent diabetes mellitus. *Nature* 329:599, 1987). Comparisons of these sequences indicates that any given DQA1 or DQB1 homozygous or heterozygous allelic combination is characterized by a specific sequencing ladder.

Total RNA from PBMNCs from 40 different subjects was tested to evaluate if the allelic composition of DQA1 and DQB1 homo- and heterozygotes could be determined correctly by direct amplification and sequencing using Type 1 primers. These subjects had been previously serologically typed but the typing information was not known to the investigator who assigned the Class II allelic specificities from the sequencing results. These 40 subjects comprised 27 different heterozygote combinations (Table III). All individuals were assigned DQA1 and DQB1 allelic sequences that were consistent with the serological phenotypes. In all the heterozygotes tested, both allelic sequences could be read clearly from the composite sequence pattern. A unique pattern is found for every particular heterozygote combination in the same way that certain RFLP banding patterns correspond to certain heterozygote allelic combinations. For instance, in a DQB2/DQB1.1 heterozygote one would find the sequence GGGG(A/T)T(T/A)CCGGGC(A/G) at codons 45 to 49 which can only be attributed to that particular allele combination. In practice, interpretation of heterozygous sequence ladders is initiated by reading certain polymorphic positions where allele-specific bases may be found, such as, for instance, the second base of codon 46, where DQB1*0201 is the only allele that has an A. The sequences of the two possible templates are then deduced and compared with the sequences of all known alleles at the different loci.

The absence of expected bands or the presence of unexpected bands for a particular allele or allelic combination is therefore suggestive of sequence heterogeneity, i.e., new alleles. The same can be said for DPA1 and DPB1 typing when appropriate primer combinations are used (Table III). For instance, substitution of the A at the second base of codon 46 would strongly suggest the presence of a sequence variant of DQB1*0201. Once detected, the sequence of the variant can be confirmed after selective amplification of the variant or by subcloning the amplified products.

3. Amplification and Direct Sequencing of DRB cDNAs from Subjects of Unknown HLA Type As described above, the use of Type 1 primers allows the unambiguous sequencing of all heterozygous combinations of DQA1 and DQB1 alleles. The same can be said for DPA1 and DPB1 typing when appropriate primer combinations are used (Table II). Because of the isotypic complexity of DRB genes (expression of more than one DRB locus by certain haplotypes), amplification and sequencing of cDNAs from DRB heterozygotes with Type 1 primers can generate up to four overlapping ladders, thus generating complex sequencing patterns.

DRB cDNAs from the same 40 individual tested above for DQA1 and DQB1 genes were amplified and sequenced using DRB-specific Type 1 primers. As mentioned above, these 40 individuals comprised 27 different heterozygote combinations, including several examples from each of the groups of complex DRB allelic combinations which would generate up to four sequencing ladders. The DRB sequence ladders generated with Type 1 primers were analyzed as described above for DQA1 and DQB1 loci: highly polymorphic positions were analyzed first for the presence of bands unique to specific alleles or groups of alleles (i.e., DR4) and the sequences deduced and compared with the sequences of all known alleles at all loci. As an example, in Table III we show data from the ladder generated by sequencing a complex DRB heterozygote (four overlapping ladders). For all but one sample, the information deduced from these sequencing experiments matched the independently determined serological phenotypes of the subject under study as well as the DQA1 and DQB1 allelic types assigned to these individuals by direct sequencing of these genes as described above. The inconsistent sample had been serologically typed as DRw13/DR4 but was typed by sequence analysis as DRw13/DRw8-Dw8.1. The presence of a DRB1*0801 allele instead of a DRB1*0401 allele was confirmed in a repeated experiment; we thus believe that the serological typing was in error. In all the 40 cases, all DQB1, DQA1 and DRB1 templates had been equally amplified and sequenced with a similar efficiency by the use of Type 1 primers. DRB3, DRB4 and DRB5 sequence ladders could be read in all but one case (a DRB3*0101 [DRw52a] sequence was not initially observed in a DRw13/DRw17 heterozygote). Since DRB3*0101 is in linkage disequilibrium with DRB1*0301, the former allele was expected to be found in the overlapping ladder as well. In order to rule out the possibility of an error, the investigator assigning the HLA types from the sequencing ladders repeated the typing of this individual; the DRB3*0101 could be read in the repeated experiment.

Although the results generated by the use of Type 1 primers were compatible with the serological phenotypes, the exclusive use of Type 1 primers will not allow in all cases to assign each of the specific ladders to each of the expressed loci in all possible heterozygotes. Given below are the most complex situations which cannot be addressed by the exclusive use of Type 1 primers: 1) distinction among the different DR4 allelic sequences in certain heterozygotes since they differ by only a few nucleotide base pairs and such differences could be masked by the presence of additional ladders; 2) to distinguish between DRB1*1601 and DRB1*1502 since their sequence differences will be masked by those of their linked DRB5 alleles; 3) to distinguish between DRB1*1301 and DRB1*1302 (which only differ at codon 86 since this difference can also be masked by other ladders; and finally 4) distinction between DRB1*0301 and DRB1*0302 in specific heterozygote combinations.

We have thus developed a more informative strategy to deal with DRB; this strategy, which consists of the additional use of non-conserved (Type 2) primers permits the clear elucidation of even the most complex combination of the four DRB sequences that might be present in an individual. These non-conserved primers, as opposed to allele-specific primers, are designed to be used in reactions performed simultaneously with the reactions using Type 1 primers and aim at selectively amplifying certain ladders from the complex sequencing patterns without requiring previous typing information.

Analysis of the sequence variability of the second exon of the DRB genes has allowed us to identify two regions which could be used to design non-conserved (Type 2) primers: 1) codons 5–13; and 2) codons 29–35. The sequence of the former region follows a group-specific sequence pattern, i.e., a sequence shared by groups of alleles at individual loci. The later region exhibits a scattered nucleotide polymorphism in DRB1 and DRB3, DRB4 and DRB5 genes. We designed five different non-conserved primers annealing to these two polymorphic regions: 1) DRB23 (specific for DR2-DRB1 ladders); 2) DRB24 (specific for DRw17-, DRw18-, DRw13-, DRw14-, DRw11-, DRw12-, and DRw8- DRB1 ladders); 3) DRB25 (specific for DR4- DRB1 ladders); 4) DRB16 and 5) DRB17, the latter two primers annealing to the second region of moderate polymorphism (from 1 to 5 nucleotides different among the known alleles for each locus) (Tables I and IV). Because of the different nature and distribution of mismatches between these primers and the different DRB templates, the type of templates amplified selectively by these primers will be different. Each of the first three primers will amplify up to two DRB1 cDNAs in any given heterozygote and will not amplify any DRB3, DRB4 or DRB5 cDNAs. On the contrary, the use of primers DRB16 and DRB17 will allow the random selective amplification of certain transcripts from DRB1, DRB3, DRB4 and/or DRB5 loci in most heterozygote combinations. We therefore tested these primers in order to determine which combination would give the best discriminatory results for DRB typing. Furthermore, since the sequences of these primers carry from 0–12 mismatches with the sequences of the known DRB alleles at the different DRB loci, their use allowed us to determine the number of mismatches between the primers and each of the possible cDNAs that are required to obtain such selective amplification of DRB transcripts. The specific combinations of primers used for the cDNA/PCR/sequencing reactions are shown in Table II above. The results of this analysis are shown below.

TABLE IV

Contribution of Nucleotide Base Pair Mismatches Between 5' Amplification Primers and DRB Alleles to the Selective Amplification of Allelic And/or Non-Allelic DRB Transcripts Table IIIa. Mismatches between Type 2 DRB-primers and DRB alleles at different loci.

| | DRB1 | | | | | | | | |
|---|---|---|---|---|---|---|---|---|---|
| | *0101–3 | *1501 | *1601–2 *1502 | *1401–2 *0301/1301–2 | *0401–8 | DR5x6## *1101–4 | *0801–3 | *1201 | *0701 |
| DRB16 | 0 | 2 | 1 | 4 | 3 | 2 | 3 | 5 | 4 |
| DRB17 | 4 | 4 | 5 | 0 | 3 | 2 | 3 | 1 | 3 |
| DRB23 | 5 | 0 | 0 | 7 | 4 | 4 | 7 | 8 | 8 |
| DRB24 | 6 | 5 | 5 | 0 | 4 | 0 | 0 | 0 | 12 |
| DRB25 | 6 | 4 | 4 | 8 | 0 | 8 | 8 | 8 | 5 |

| | DRB1 | | | DRB3/DRB4/DRB5 | | | |
|---|---|---|---|---|---|---|---|
| | *0901 | *1001 | DRB5# | DRB3*0101 | DRB3*0201 | DRB3*0301 | DRB4 |
| DRB16 | 1 | 3 | 3 | 4 | 5 | 4 | 2 |
| DRB17 | 5 | 4 | 1 | 0 | 1 | 0 | 2 |
| DRB23 | 2 | 4 | 6 | 5 | 5 | 5 | 3 |
| DRB24 | 5 | 4 | 6 | 5 | 5 | 5 | 3 |
| DRB25 | 5 | 4 | 8 | 6 | 5 | 5 | 4 |

DRB5 gene from cell line AMAI has an additional nucleotide substitution in the first base of codon 30, in comparison with DRB5 genes of other DR2 haplotypes.
The DRB1 gene of this specificity (DR5x6) has been given this arbitrary designation according to serological, RFLP and sequence information.

TABLE V

Selective Amplification of DRB and DQB1 cDNAs
In Combinations of Alleles Mismatched with
Type 2 Oligonucleotides(#)

| Haplotypes | Selected Alleles | DO Primer |
|---|---|---|
| DRB1*1301,DRB3*0101/DRB1*1601,DRB5*0201 | DRB1*1601 | DRB16 |
| DRB1*1301,DRB3*0101/DRB1*0801 | DRB1*0801 | DRB16 |
| DRB1*0301,DRB3*0101/DRB1*1601,DRB5*0201 | DRB1*1601 | DRB16 |
| DR5x6,DRB3*0101/DRB1*0801 | DRB1*0801 | DRB16 |
| DR5x6,DRB3*0101/DRB1*08011 | DRB3*0101 | DRB17 |
| DR5x6,DRB3*0101/DRB1*0301,DRB3*0101 | DR5x6 | DRB16 |
| DRB1*1101,DRB3*0201/DRB1*1501,DRB5*0101 | DRB3*0201 | DRB16 |
| DRB1*1101,DRB3*0201/DRB1*1501,DRB5*0101 | DRB5*0101 | DRB17* |
| DRB1*1201,DRB3*0201/DRB1*1101,DRB3*0201 | DRB1*1101 | DRB16 |
| DRB1*1201,DRB3*0201/DRB1*1101,DRB3*0201 | DRB1*1201 + DRB3*0201 | DRB17 |
| DRB1*0405,DRB4*0101/DRB1*0301,DRB3*0101 | DRB1*0405 + DRB4*0101 | DRB16 |
| DR5x6,DRB3*0101/DRB1*1101,DRB3*0201 | DRB1*1101 + DR5x6 | DRB16 |
| DRB1*1501,DRB5*0101 | DRB1*1501 | DRB16 |
| DRB1*1601,DRB5*0201/DRB1*0401,DRB4*0101 | DRB1*0401 + DRB5*0201 | DRB17 |
| DRB1*1601,DRB5*0201/DRB1*0401,DRB4*0101 | DRB1*1601 + DRB1*0401 | DRB16** |
| DRB1*1601,DRB5*0201 | DRB1*1601 | DRB16 |
| DRB1*1601,DRB5*0201 | DRB5*0201 | DRB17 |
| DRB1*1602,DRB5*0202 | DRB1*1602 | DRB16 |
| DRB1*0401,DRB4*0101 | DRB4*0101 | DRB16 |
| DQB1*0604/DQB1*0502 | DQB1*0604 | DQB6 |
| DQB1*0301/DQB1*0101 | DQB1*0301 | DQB6 |
| DQB1*0301/DQB1*0101 | DQB1*0501 | DQB14 |
| DQB1*0201/DQB1*0603 | DQB1*0201 | DQB6 |
| DQB1*0604/DQB1*0301 | DQB1*0604 | DQB15 |
| DQB1*0301/DQB1*0502 | DQB1*0301 | DQB6 |
| DQB1*0603/DQB1*0101 | DQB1*0603 | DQB6 |
| DQB1*0603/DQB1*0101 | DQB1*0501 | DQB14 |
| DQB1*0201/DQB1*0101 | DQB1*0501 | DQB14 |
| DQB1*0201/DQB1*0302 | DQB1*0201/DQB1*0302 | DQB6*** |
| DQB1*0201/DQB1*0502 | DQB1*0201 | DQB6 |

(#) In this Table we only show representative examples of haplotypic combinations lacking those alleles the primers are fully matched with, for reasons of simplicity (see Table IV). Whenever these primers were used in heterozygotes carrying the alleles they specifically recognize, these alleles were selectively amplified. Note that in the examples shown in the Table the non-conserved primers selectively amplified the templates closer in sequence to the primer. The DRB and DQB1 alleles composing these haplotypes are shown under "haplotypes". The selected alleles and the primers used are indicated in the two other columns. More than one individual was tested for some of the heterozygote combinations listed in this Table.
*DRB5*0101 and DRB3*0201 templates both have one mismatch with primer DRBI17. Selection of DRB5*0101 could be related to the differential positioning of the mismatch with respect to the primer.
**A Weaker DRB4*0101 template was also observed.
***Despite the presence of a mismatch between these two DQB1 alleles, primer DODQB6 was not able to select either of them.

These primers were able to selectively amplify certain DRB templates in all the heterozygous combinations tested. In heterozygotes carrying the alleles these primers are matched with, these alleles were selectively amplified; in heterozygotes not carrying the alleles specifically recognized by the primers, the DRB templates which had the fewest base pair mismatches with the primers were selectively amplified in the PCR. Specific examples of the latter are shown in Table V. As shown in Table V, Type 2 primers could differentially amplify DRB transcripts from the combinations of allelic cDNAs that differ from each other in as few as one nucleotide substitution, provided that high stringency annealing conditions are used for the PCR (annealing at 55° C.). For example, in the heterozygote combination DRw13/DRw8–Dw8.1, the DRB1*0801 allele (3 mismatches with the primer) was selected over DRB1*1301 and DRB3*0101 genes (each has 4 mismatches with the primer) by the DRB16 oligonucleotide primer. Although DRB3*0101 or DRB3*0201 and DRB5*0101 genes all harbour one mismatch with primer DRB17, this oligonucleotide selected the DRB5*0101 sequence in a DRw11/DRw15 heterozygote (Table V). It is possible that the differential positioning of the mismatches within the sequence recognized by the oligonucleotide also has an influence on the stability of the primer/cDNA complex and hence on the outcome of the PCR.

The ability of non-conserved primers to select certain alleles in heterozygote combinations was also tested for DQB1 genes (Table V). As with DRB-specific Type 2 primers, the use of high temperatures (55° C.) in the annealing step of the PCR was required for achieving the selective amplification of single DQB1 alleles in heterozygotes with non-conserved primers. For instance, when annealing of primer DQB6 was allowed to proceed at 37° C. in cDNAs from a DQB1*0301/DQB1*0501 and a DQB1*0201/DQB1*0603 heterozygote, both alleles in both heterozygotes were equally amplified. At 55° C., the allele with the most homologous sequence to the 5' primer, was amplified over the other in the PCR. Combinations of alleles both differing from the primer in two nucleotides but in different relative position were also differentially amplified with a non-conserved primer. For instance, primer DQB6 selected the DQB1*0604 sequence in a DQB1*0604/DQB1*0502 heterozygote (Table V). Five nucleotides separate the two mismatches between the DQB1*0604 allele and the DQB6 primer, whereas only two nucleotides separate the mismatches between the DQB1*0502 and the primer.

These results clearly indicate that the oligonucleotide primers annealing to polymorphic regions at the 5' end of the target cDNAs can be tailored to achieve a reproducible selective amplification of a limited number of DRB or DQB templates in complex heterozygous combinations. Although the use of Type 1 primers allows the unambiguous sequencing of all possible DQA, DQB, DPA and DPB heterozygotes, such an approach will not give absolute discriminatory information for all DRB heterozygotes. We have shown that the simultaneous use of Type 1 and Type 2 primers for DRB will permit the clear elucidation of even the most complex of all DRB heterozygote combinations. When DRB-SBT is used for typing purposes, we perform three Type 2-reactions (using DRB23, 24 and 25) simultaneously with a Type 1-reaction (Table II). The simultaneous use of these reactions using these primers has the highest discriminatory power for complete DRB typing in a single run and allows the identification of novel sequence heterogeneity. Only one Type 1 reaction is required for DQB1, one for DQA1, one for DPA1 and one for DPB1 (Table II).

EXAMPLE III

Figure 2A:
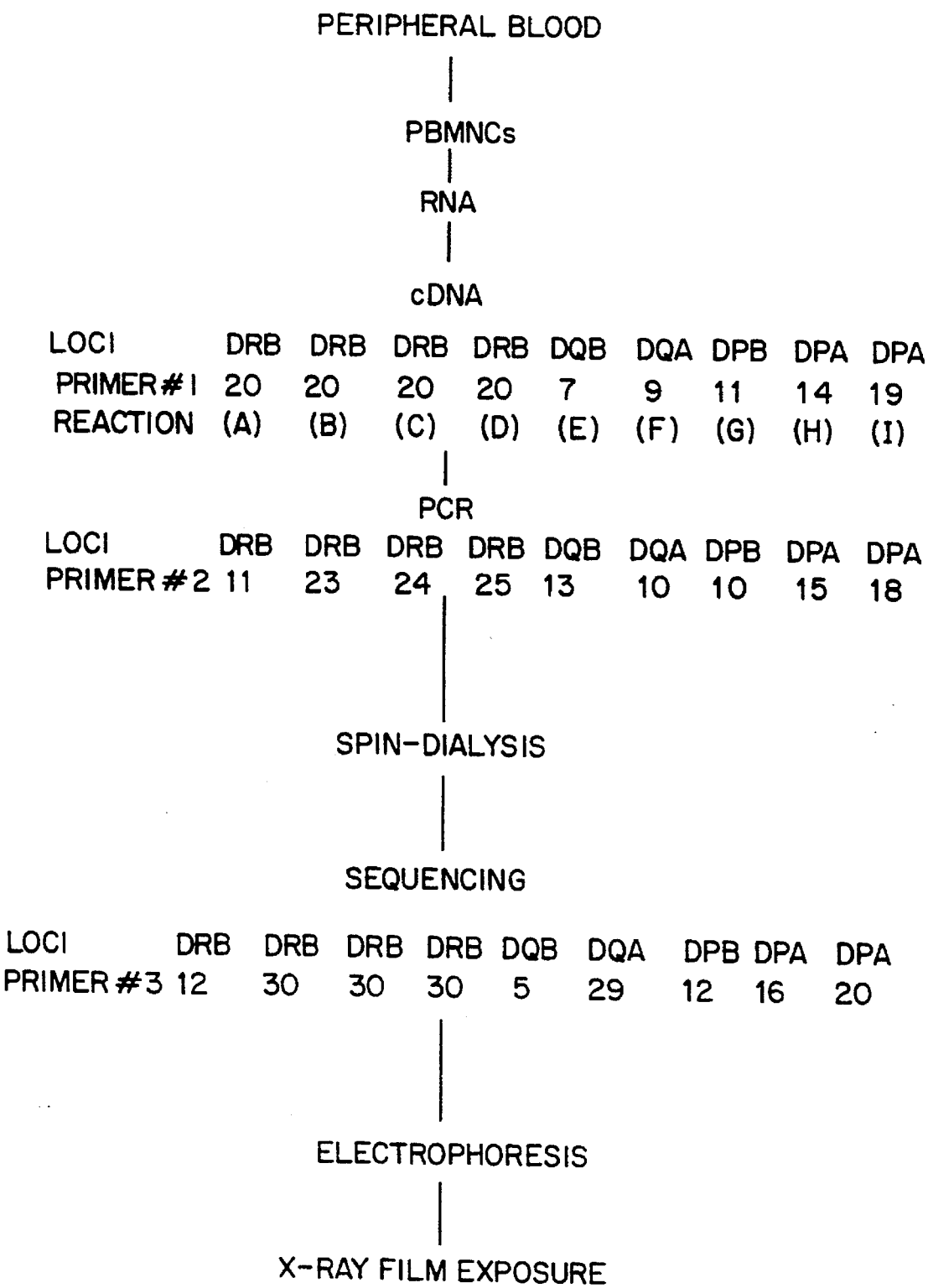
FIG. 2A shows a flow-chart of the procedure for peripheral blood samples. Each reaction is performed in a different test tube. The reactions are named with capital letter in parenthesis; these letters correspond to those shown in Table II (combinations of primers/reaction). Only the "routine" combinations of primers are shown in this Figure.
Figure 2B:
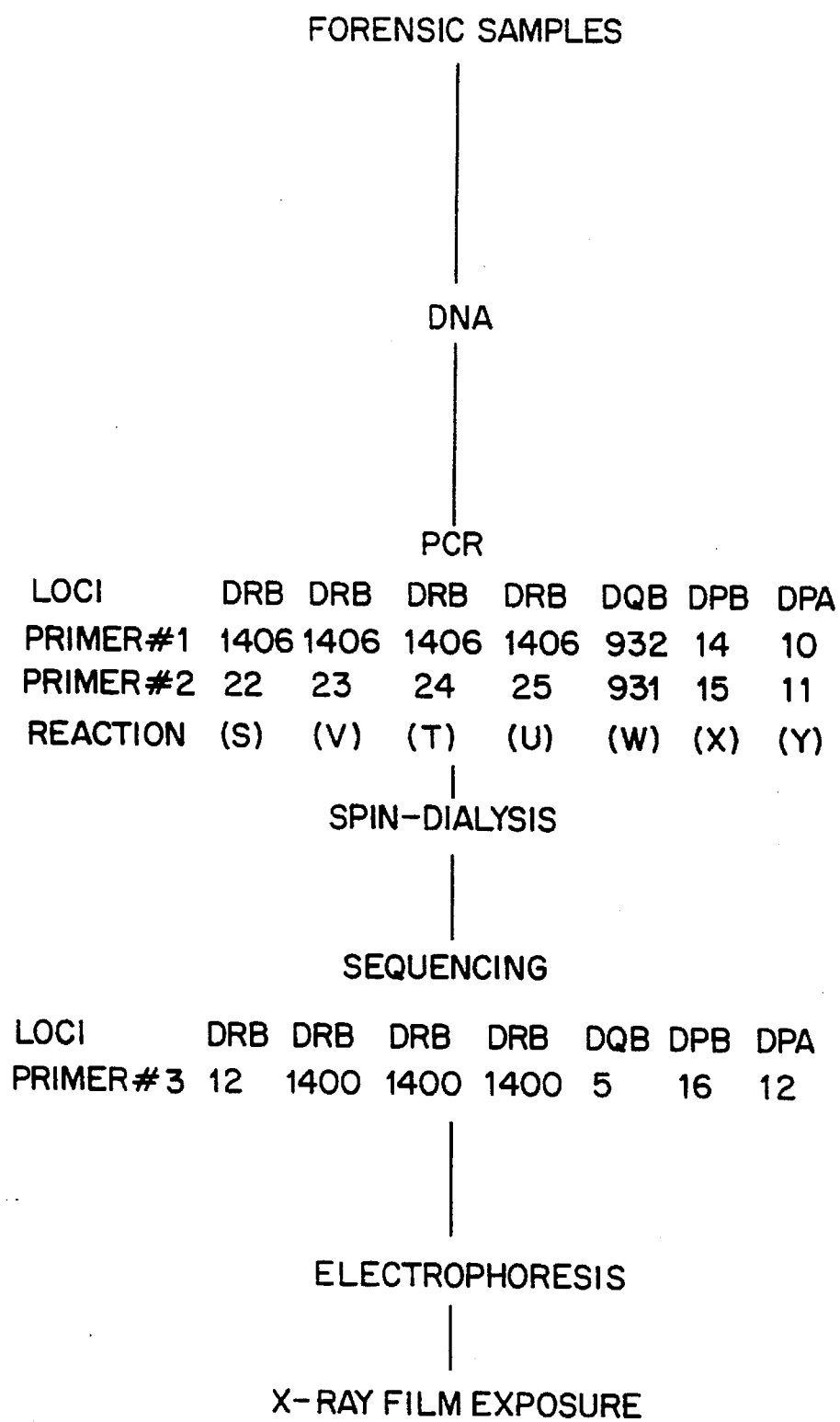
FIG. 2B is a flow-chart of the procedure for forensic samples, where DNA iis usually the only available genetic material to work with. DNA in these situations is usually isolated from hair, sperm, blood stains, etc. The combinations of primers per reaction shown in the Figure correspond to the "routine" combinations only.

Determining Unknown HLA Type of Subjects by Direct Sequencing of the Second Exon of Class II Genes Routine HLA typing of large populations of individuals for sequence polymorphisms can be performed by the use of the methodology reported here which can also identify previously unknown allelic variants. FIGS. 2A and 2B show a flow-chart for the routine protocol used to determine sequence allelism of individuals of unknown HLA types.

1. Employment of Primer Combinations for cDNA, PCR and Direct Sequencing Using RNA as Initial Template For synthesizing cDNA molecules, the present invention provides single strand DNA anti-sense oligonucleotide primers that anneal to conserved regions of the gens mRNAs to be reverse transcribed, amplified and sequenced. These oligonucleotide primers include an oligonucleotide sequence that: (1) anneals to a conserved region (codons 105 through 111) shared by all the alleles at all the DRB loci, the latter being DRB1, DRB3, DRB4 and DRB5, respectively (e.g., primer DRB20). Four simultaneous cDNA reactions (one per tube) are performed for DRB typing, all using primer DRB20 (reactions A, B, C and D in Table II and FIG. 2A); (2) anneals to a conserved region (codons 105 through 111) shared by all the alleles at the DQB locus (e.g. primer DQB7) (reaction E in Table II and FIG. 2A); (3) anneals to a conserved region (codons 147 through 157) shared by all the alleles at the DQA locus (e.g. primer DQA9) (reaction F in Table II and FIG. 2A); (4) anneals to a conserved region (codons 105 through 111) shared by all the alleles at the DPB locus (e.g. primer DPB11) (reaction G in Table II and FIG. 2A); (5) anneals to a conserved region (codons 104 through 110) shared by all the alleles at the DPA locus (e.g. primer DPA14) (reaction H in Table II and FIG. 2A); (6) anneals to a conserved region (codons 222 through 228) shared by all the alleles at the DPA locus (e.g. primer DPA19) (reaction I in Table II and FIG. 2A). The specific oligonucleotides added to each of these reactions once the cDNA synthesis is done in order to amplify and sequence the products are indicated below as well as in Table II and in FIG. 2.

To amplify cDNA molecules corresponding to each expressed DRB loci of each chromosome (DRB1 and DRB3 or DRB4 or DRB5, depending on the haplotype -isotypic complexity-), a conserved oligonucleotide primer which anneals to codons −32 to −26 (e.g. oligonucleotide DRB11) is added to one of the four tubes where the cDNA synthesis reactions corresponding to DRB genes took place. The combination of the cDNA synthesis reaction primer and the newly added conserved primer is used to amplify all the alleles at all DRB loci expressed by a given individual. Each of the remaining three tubes containing DRB cDNA products receives one of three different non-conserved oligonucleotides (also called Type 2) annealing to codons 7–13 (e.g. primer DRB23), 5–11 (e.g. primer DRB24), 6–13 (e.g. primer DRB25), respectively. Each non-conserved primer is designed to favor the amplification of cDNAs corresponding to different groups of alleles at the DRB1 locus. Comparison of the sequencing ladders generated by these four reactions allows complete and accurate interpretation of the sequences corresponding to each of the four possible DRB genes expressed by a given individual (one or two for each of the parental chromosomes).

For the DQB1 locus, a conserved oligonucleotide primer which anneals to codons 1–7 of the DQB cDNAs (e.g. primer DQB13) can be used for amplifying each of the DQB1 genes expressed in any given individual (one for each parental chromosome). In the case of the DQA1 locus, a conserved single strand DNA oligonucleotide primer useful for amplifying each of the DQA1 genes expressed in any given subject anneals to codons −10 to −4 of the DQA1 cDNA (e.g. primer DQA10). For the DPB1 locus, a conserved oligonucleotide (e.g. primer DPB10) annealing to codons −19 to −13, is used to amplify each of the expressed DPB1 genes in any given subject. For DPA1 locus, a conserved oligonucleotide (e.g. primer DPA15) annealing to codons −23 to −17, is used to amplify each of the expressed DPA1 genes in a given subject. Inca separate reaction, conserved primer DPA18, annealing to codons 59–65 of the DPA1 cDNAs is used in combination with the cDNA primer DPA19 to amplify each of the expressed DPA1 genes in any individual. This second DPA1 reaction is targeted at a second polymorphic region of this gene.

Primers useful in direct sequencing the polymerase chain reaction products corresponding to DRB loci include an anti-sense oligonucleotide primer (e.g. DRB12) annealing to codons 87–94 of all the alleles at DRB loci; this primer is used for sequencing the products generated by the first of the four DRB reactions. For direct sequencing the polymerase chain reaction products generated with the other three DRB reactions, an anti-sense oligonucleotide annealing to codons 97–103 of all the alleles at DRB1 locus can be used (e.g. primer DRB30). The use of a different sequencing oligonucleotide in these three DRB reactions allows reading of downstream polymorphic regions of DRB1 genes not seen in the first DRB reaction which uses the example sequencing primer DRB12. Primers useful in direct sequencing the polymerase chain reaction products corresponding to DQB1 locus include an anti-sense oligonucleotide primer (e.g. DQB5) annealing to codons 78–83 of all the alleles at this locus. Direct sequencing of polymerase chain reaction products corresponding to DQA1 locus include an anti-sense oligonucleotide primer (e.g. DQA29) annealing to codons 88–95 of all the alleles at this locus. Direct sequencing of polymerase chain reaction products corresponding to DPB1 locus include an anti-sense oligonucleotide primer (e.g. DPB12) annealing to codons 97–103 of all the alleles at this locus. For direct sequencing of polymerase chain reaction products for the DPA1 reaction which used primers DPA14 and DPA15, an anti-sense oligonucleotide annealing to codons 88–94 of all the alleles at this locus can be used (e.g. primer DPA16). For direct sequencing of polymerase chain reaction products for the DPA1 reaction which used primers DPA19 and DPA18, an anti-sense oligonucleotide annealing to codons 214–220 of all the alleles at this locus can be used (e.g. primer DPA20).

2. Employment of Primer Combinations for PCR and Direct Sequencing Using DNA Templates To amplify DNA molecules corresponding to each DRB loci of each chromosome a conserved anti-sense oligonucleotide primer annealing to base pairs 18–38 of intron 3 (e.g. oligonucleotide DRB1406) is added to each of four PCR reaction tubes (reactions S, V, T and U in Table II and FIG. 2B). Each of these four tubes will receive a different additional oligonucleotide annealing to codons −4 to +3 (e.g. primer DRB22), to codons 7–13 (e.g. primer DRB23), 5–11 (e.g. primer DRB24), 6–13 (e.g. primer DRB25), respectively. The first reaction is used to amplify all the alleles at all DRB loci carried by a given individual. Each of the remaining three reactions is designed to favor the amplification of DNA corresponding to different groups of alleles at the DRB1 locus. As with RNA templates, comparison of the sequencing ladders generated by these four reactions allows complete and accurate interpretation of the sequences corresponding to each of the four possible DRB genes expressed by a given individual (one or two for each of the parental chromosomes).

For the DQB1 locus, two conserved oligonucleotide primers which anneal to codons 88–94 (e.g. primer DQB932) and 11–17 (e.g. primer DQB931) or 1–7 (e.g. primer DQB13) can be used for amplifying each of the DQB1 genes carried by any given individual (one for each parental chromosome) (reaction W in Table II and FIG. 2B). For the DPB1 locus, two conserved oligonucleotides (a primer, e.g. DPB14, annealing to base pairs −42 to −62 of intron 2, and a primer e.g. DPB15, annealing base pairs 39–59 of intron 3) are used to amplify each of the DPB1 genes carried by any given subject (reaction X in Table II and FIG. 2B). For DPA1 locus a conserved oligonucleotide such as DPA10 (annealing to base pairs −69 to −50 of intron 2) and DPA11 (annealing to base pairs 55–71 of intron 3) are used to amplify each of the DPA1 genes carried by a given subject (reaction Y in Table II and FIG. 2B).

Primers useful in direct sequencing the polymerase chain reaction products generated from DNA templates corresponding to DRB loci include an anti-sense oligonucleotide primer (e.g. DRB12) annealing to codons 87–94 of all alleles at DRB loci; this primer is used for sequencing the products generated by the first of the four DRB reactions. For direct sequencing the polymerase chain reaction products generated with the other three DRB reactions, a sense oligonucleotide annealing to codons 39–46 of all the alleles at DRB1 locus can be used (e.g. primer DRB1400). The use of a different sequencing oligonucleotide in these three DRB reactions allows reading of downstream polymorphic regions of DRB1 genes not seen in the first DRB reaction which uses the example sequencing primer DRB12. Primers useful in direct sequencing the polymerase chain reaction products corresponding to DQB1 locus include an anti-sense oligonucleotide primer (e.g. DQB5) annealing to codons 78–83 of all the alleles at this locus. Direct sequencing of polymerase chain reaction products corresponding to DPB1 locus include an anti-sense oligonucleotide primer (e.g. DPB16) annealing to base pairs 1–21 of intron 3 of all the alleles at this locus. For direct sequencing of polymerase chain reaction products for the DPA1 reaction an anti-sense oligonucleotide annealing to codons 76–82 of all the alleles at this locus can be used (e.g. primer DPA12).

Procedure for Determining Unknown HLA Type

A subject of unknown HLA type, diseased or not, is to be typed for Class II HLA polymorphism. From 10 to 50 mL of peripheral blood are drawn. The peripheral blood mononuclear cells are prepared by centrifugation over Ficoll-Hypaque gradients. The cells are then lysed in guanidium isothyocianate and total cellular RNA prepared using conventional methods (either by centrifugation on cesium chloride gradients, which lasts about 16 hours, or by the guanidium isothyocianate-phenol-chlorophorm extraction method, which can be performed in less than 4 hours. See Gouuh, supra (1988); Johns et al., *Anal. Biochem.*, 180:276 (1989). Otherwise genomic DNA from these cells or other sources (hair, blood stains, sperm, etc.) can be prepared by conventional methods such as provided by Higuchi, R. in *PCR Technology,* Erlich, M. (ed.), Stockton Press:31 (1989). DQB1, DQA1, DRB (DRB1, DRB3/4/5), DPA1 and DPB1 cDNA molecules are synthesized from total RNA using locus-specific primers. Approximately, one microgram of RNA is reverse transcribed with MoLVRT (reverse transcriptase) and DRB (CODRB20), DQB (CODQB7), DQA (CODQA9), DPB (DPB11) and DPA (DPA14, DPA19) (optional) -specific non-sense primers in a 20 uL final volume reaction (30–60 minute incubation). The reaction for each Class II gene is performed in a different tube, but they can be performed in the same tube if preferred. For routine purposes, four simultaneous reactions are performed for DRB, one for DQB, one for DQA1, one for DPB1, and two for DPA1 gene products.

Once these reactions are completed, the enzymatic amplification of the respective cDNA molecules is then performed by directly adding to the 20 uL reverse transcription reaction, the reagents needed for the amplification step. Alternatively, if DNA is used, the primer combinations used for the PCR are those shown in Table II herein (the anti-sense primers as well as the sense primers will be different). This includes the PCR reagents and appropriate conserved and non-conserved oligonucleotide primers. This example uses four reactions for DRB (tubes 1, 2, 3 and 4), one for DQB (tube 5), one for DQA (tube 6), one for DPR (tube 7), and two for DPA (tubes 8 and 9, respectively). Reactions 2, 3 and 4 incorporate primers DRB23, DRB24 and DRB25, respectively. For rapid typing (in less than 24 hours), the latter are the preferred combinations. Alternative combinations of the primers that can be used are shown in Table II.

Once completed, the reactions are spun-dialyzed for about 15 minutes using Centricon (Amicon, Ultrafree (millipore)) or similar columns to remove unincorporated primers and dNTPs. The retentate or one half of the recovered retentate for each reaction is then directly sequenced using Taq polymerase and the primers described in Table II for each combination of primers used in the cDNA/PCR reactions using P-32 end-labeled (10 minutes) locus-specific sequencing primers (35 minutes).

The sequencing reactions products are loaded on an acrylmide gel, electrophoresed in 2–3 hours and exposed to X-ray films for 4–12 hours. The gels are read and results from gels are compared to nucleotide sequences corresponding to all possible alleles.

Comparisons can be made visually using the naked eye or using a personal computer and a software package including the nucleotide sequences of all alleles of all haplotypes and routines which indicate how the comparison is to be performed as well as subroutines which will allow identification of new allelic sequences.

What is claimed:

1. A method for determining a nucleotide sequence of a Class II HLA-DRB gene locus of a subject in a sample containing subject RNA, said method comprising:

(a) synthesizing, from RNA isolated from said sample, a cDNA molecule for each allele of said gene locus using in a synthesis reaction an oligonucleotide antisense primer depicted in SEQ. ID. NO:2 to produce a cDNA molecule;

(b) amplifying in four separate amplification reactions said cDNA molecule to generate sufficient first and second double stranded amplification reaction products respectively for sequencing each allele of said gene locus using in the first amplifying reaction an oligonucleotide primer depicted in SEQ. ID. NO:2 and an oligonucleotide primer depicted in SEQ. ID NO:6 using an amplification temperature of 37° C. and in the second amplifying reaction an oligonucleotide primer depicted in SEQ. ID NO: 2 and an oligonucleotide primer depicted in SEQ. ID NO: 42 and in the third amplifying reaction an oligonucleotide primer depicted in SEQ. ID NO: 2 and an oligonucleotide primer depicted in SEQ. ID NO: 43 and in the fourth amplifying reaction an oligonucleotide primer depicted in SEQ. ID NO: 2 and an oligonucleotide primer depicted in SEQ. ID NO: 44;

(c) sequencing directly each first and second amplifying reaction product to produce at least one sequencing ladder for each amplifying reaction product using in a sequencing reaction oligonucleotide primer depicted in SEQ. ID. NO:11 or an oligonucleotide primer depicted in SEQ. ID. NO:13 or SEQ ID NO:5 and;

(d) analyzing each sequencing ladder to determine the nucleotide sequence of said HLA-DRB gene locus.

2. A method for determining a nucleotide sequence of a Class II HLA-DRB gene locus of a subject in a sample containing subject RNA, said method comprising:

(a) synthesizing, from RNA isolated from said sample, a cDNA molecule for each allele of said gene locus using in a synthesis reaction an oligonucleotide antisense primer depicted in SEQ. ID NO:2 to produce a cDNA molecule;

(b) amplifying in six separate amplification reactions said cDNA molecules to generate sufficient first and second double stranded amplification reaction products respectively for sequencing each allele of said gene locus using in the first amplifying reaction an oligonucleotide primer depicted in SEQ. ID. NO:2 and an oligonucleotide primer depicted in SEQ. ID. NO:6 at about 37° C. and in the second amplifying reaction an oligonucleotide primer depicted in SEQ. ID NO:2 and an oligonucleotide primer depicted in SEQ ID NO:42 and in the third amplifying reaction an oligonucleotide primer depicted in SEQ. ID. NO:2 and an oligonucleotide primer depicted in SEQ. ID. NO:44 and in the fourth amplifying reaction an oligonucleotide primer depicted in SEQ. ID. NO:2 and an oligonucleotide primer depicted in SEQ. ID. NO:43 and in the fifth amplifying reaction an oligonucleotide primer depicted in SEQ. ID. NO:2 and an oligonucleotide primer depicted in SEQ. ID. NO:45 and in the sixth amplifying reaction an oligonucleotide primer depicted in SEQ. ID. NO:2 and an oligonucleotide primer depicted in SEQ. ID. NO:46;

(c) sequencing directly each first and second amplifying reaction product to produce at least one sequencing ladder for each amplifying reaction product using in a sequencing reaction an oligonucleotide primer depicted in SEQ. ID. NO:11 or an oligonucleotide primer depicted in SEQ. ID. NO:13; and (d) analyzing each sequencing ladder to determine the nucleotide sequence of said HLA-DRB gene locus.

3. A method for determining a nucleotide sequence of a Class II HLA-DQA gene locus of a subject in a sample containing subject RNA, said method comprising:

(a) synthesizing, from RNA isolated from said sample, a cDNA molecule for each allele of said gene locus using in a synthesis reaction an oligonucleotide antisense primer depicted in SEQ. ID NO:3 to produce a cDNA molecule;

(b) amplifying said cDNA molecule to generate sufficient first and second double stranded amplification reaction products respectively for sequencing each allele of said gene locus using in an amplifying reaction an oligonucleotide primer depicted in SEQ. ID. NO:3 and an oligonucleotide primer depicted in SEQ. ID. NO:7;

(c) sequencing directly each amplifying reaction product to produce at least one sequencing ladder for each amplifying reaction product using in a sequencing reaction an oligonucleotide primer depicted in SEQ. ID. NO:14 or an oligonucleotide primer depicted in SEQ. ID. NO:15;

(d) analyzing each sequencing ladder to determine the nucleotide sequence of said HLA-DQA gene locus.

4. A method for determining a nucleotide sequence of a Class II HLA-DQB gene locus of a subject in a sample containing subject RNA, said method comprising:

(a) synthesizing, from RNA isolated from said sample, a cDNA molecule for each allele of said gene locus using in a synthesis reaction an oligonucleotide antisense primer depicted in SEQ ID NO:1;

(b) amplifying said cDNA molecule to generate sufficient first and second double stranded amplifying reaction products respectively for sequencing each allele of said gene locus using in an amplifying reaction an oligonucleotide primer depicted in SEQ ID NO:1 and an oligonucleotide primer depicted in SEQ ID NO:4;

(c) sequencing directly each first and second amplifying reaction product to produce at least one sequencing ladder for each amplifying reaction product using in a sequencing reaction an oligonucleotide primer depicted in SEQ ID NO:10 or an oligonucleotide primer depicted in SEQ ID NO:12; and (d) analyzing each sequencing ladder to determine the nucleotide sequence of said HLA-DQB gene locus.

5. A method for determining a nucleotide sequence of a Class II HLA-DQB gene locus of a subject in a sample containing subject RNA, said method comprising:

(a) synthesizing, from RNA isolated from said sample, a cDNA molecule for each allele of said gene locus using in a synthesis reaction an oligonucleotide antisense primer depicted in SEQ. ID NO:1 to produce a cDNA molecule;

(b) amplifying said cDNA molecule in four separate amplification reactions to generate sufficient first and second double stranded amplification reaction products respectively for sequencing each allele of said gene locus using in the first amplifying reaction an oligonucleotide primer depicted in SEQ. ID. NO:1 and an oligonucleotide primer depicted in SEQ. ID. NO:47 at about 37° C. and in the second amplifying reaction an oligonucleotide primer depicted in SEQ. ID. NO:1 and an oligonucleotide primer depicted in SEQ. ID. NO:47 at about 55° C. and in the third reaction an oligonucleotide primer depicted in SEQ. ID. NO:1 and an oligonucleotide primer depicted in SEQ. ID. NO:48 and in the fourth reaction an oligonucleotide primer depicted in SEQ. ID. NO:1 and an oligonucleotide primer depicted in SEQ. ID. NO:49;

(c) sequencing directly each first and second amplifying reaction product to produce at least one sequencing ladder for each amplification reaction product using in sequencing reaction an oligonucleotide primer depicted in SEQ. ID. NO:10 or an oligonucleotide primer depicted in SEQ. ID. NO:12; and (d) analyzing each sequencing ladder to determine the nucleotide sequence of said HLA-DQB gene locus.

6. A method for determining a nucleotide sequence of a Class II HLA-DPA gene locus of a subject in a sample containing subject RNA, said method comprising:

(a) synthesizing, from RNA isolated from said sample, a cDNA molecule for each allele of said gens locus using in a first synthesis reaction an oligonucleotide primer depicted in SEQ ID NO:31 to produce a first cDNA molecule and in a second separate synthesis reaction an oligonucleotide primer depicted in SEQ ID NO:39 to produce a second cDNA molecule, (b) amplifying said first and second cDNA molecules to generate sufficient first and second double stranded amplification reaction products respectively for sequencing each allels of said gene locus using in a first amplifying reaction an oligonucleotide primer depicted in SEQ ID NO:31 and an oligonucleotide primer depicted in SEQ ID NO:32 and using in a second amplifying reaction an oligonucleotide primer depicted in SEQ ID NO:39 and an oligonucleotide primer depicted in SEQ ID NO:38;

(c) sequencing directly each first and second amplifying reaction product to produce at least one sequencing ladders for each amplifying reaction product using in the first sequencing reaction an oligonucleotide primer depicted in SEQ ID NO:33 or SEQ ID NO:34 and in the second sequencing reaction an oligonucleotide primer depicted in SEQ ID NO:40 or SEQ ID NO:41; and (d) analyzing each sequencing ladder to determine the nucleotide sequence of said HLA-DPA gens locus.

7. A method for determining a nucleotide sequence of a Class II HLA-DPB gene locus of a subject in a sample containing subject RNA, said method comprising:

(a) synthesizing, from RNA isolated from said sample, a cDNA molecule for each allele of said gene locus using in a synthesis reaction an oligonucleotide primer depicted in SEQ ID NO:24 to produce a cDNA molecule;

(b) amplifying said cDNA molecule to generate sufficient first and second double stranded amplification reaction products respectively for sequencing each allele of said gene locus using in a amplifying reaction oligonucleotide primers depicted in SEQ ID NO:23 and SEQ ID NO:24;

(c) sequencing directly each first and second amplifying reaction product to produce with at least one sequencing ladder for each amplifying reaction product using in a sequencing reaction an oligonucleotide primer depicted in SEQ ID NO:25 or SEQ ID NO:26;

(d) analyzing each sequencing ladder to determine the nucleotide sequence of said HLA-DPB gene locus.

8. A method for rapid automated determination of an HLA Class II nucleotide sequence of a gene locus of interest of a subject in a sample containing subject nucleic acid as in any of claims 4 or 3–7 comprising:

(a) isolating nucleic acid from said sample with an RNA/DNA extractor;

(c) amplifying said nucleic acid by at least one polymerase chain reaction using a thermocycler to generate sufficient first and second double-stranded amplifying reaction products for sequencing for each allele of at least one gene locus of interest;

(c) sequencing directly using an automated sequencing apparatus each first and second double stranded amplifying reaction product for each allele at each gene locus of each chromosome; and (d) analyzing said each sequencing ladder to determine the nucleotide sequence of said gene locus of interest of said subject with a computer having a data base with allelic sequence information to compare the sequence of each allele of each gene locus sequenced to known sequences for each such gene locus.

9. An oligonucleotide primer having the sequence depicted in SEQ ID NO:3.

10. An oligonucleotide primer having the sequence depicted in SEQ. ID NO:7.

11. An oligonucleotide primer having the sequence depicted in SEQ. ID. NO:2.

12. An oligonucleotide primer having the sequence depicted in SEQ, ID NO:42.

13. An oligonucleotide primer having the sequence depicted in SEQ. ID NO:43.

14. An oligonucleotide primer having the sequence depicted in SEQ. ID NO:24.

15. An oligonucleotide primer having the sequence depicted in SEQ. ID NO:39.

16. An oligonucleotide primer having the sequence depicted in SEQ. ID NO:23.

17. An oligonucleotide primer having the sequence depicted in SEQ. ID NO:32.

18. An oligonucleotide primer having the sequence depicted in SEQ. ID NO:38.

19. An oligonucleotide primer having the sequence depicted in SEQ. ID NO:31.

20. An oligonucleotide primer having the sequence depicted in SEQ. ID NO:11.

21. An oligonucleotide primer having the sequence depicted in SEQ. ID NO:14.

22. An oligonucleotide primer having the sequence depicted in SEQ. ID NO:25.

23. An oligonucleotide primer having the sequence depicted in SEQ. ID NO:33.

24. An oligonucleotide primer having the sequence depicted in SEQ. ID NO:40.

25. An oligonucleotide primer having the sequence of depicted in SEQ. ID NO:20.

26. An oligonucleotide primer having the sequence depicted in SEQ. ID NO:5.

27. An oligonucleotide primer having the sequence depicted in SEQ. ID NO:8.

28. An oligonucleotide primer having the sequence of depicted in SEQ. ID No:9.

29. An oligonucleotide primer having the sequence depicted in SEQ. ID NO:27.

30. An oligonucleotide primer having the sequence depicted in SEQ. ID NO:28.

31. An oligonucleotide primer having the sequence depicted in SEQ. ID NO:35.

32. An oligonucleotide primer having the sequence depicted in SEQ. ID NO:36.

33. An oligonucleotide primer having the sequence depicted in SEQ. ID NO:16.

34. An oligonucleotide primer having the sequence depicted in SEQ. ID NO:26.

35. An oligonucleotide primer having the sequence depicted in SEQ. ID NO:30.

36. An oligonucleotide primer having the sequence depicted in SEQ. ID NO:34.

37. An oligonucleotide primer having the sequence depicted in SEQ. ID NO:41.

38. An oligonucleotide primer having the sequence depicted in SEQ. ID NO:10.

39. An oligonucleotide primer having the sequence depicted in SEQ. ID NO:15.

* * * * *

UNITED STATES PATENT AND TRADEMARK OFFICE
CERTIFICATE OF CORRECTION

PATENT NO. : 5,578,443
DATED : November 26, 1996
INVENTOR(S): Santamaria et al.

It is certified that error appears in the above-identified patent and that said Letters Patent is hereby corrected as shown below:

Claim 6, column 64, line 52, "gens" should read --gene--.
Claim 6, column 64, line 61, "allels" should read --allele--.
Claim 6, column 65, line 3, "ladders" should read --ladder--.
Claim 6, column 65, line 9, "gens" should read --gene--.
Claim 7, column 65, line 26, "produce with at least " should read --produce at least--.
Claim 8, column 65, line 35, "4 or 3-7" should read --1-7--.
Claim 8, column 65, line 38, "(c)" should read --(b)--.

Signed and Sealed this

Eighteenth Day of January, 2000

Attest:

Q. TODD DICKINSON

*Attesting Officer*  *Commissioner of Patents and Trademarks*